(12) United States Patent
Ferber et al.

(10) Patent No.: US 12,268,495 B2
(45) Date of Patent: Apr. 8, 2025

(54) METHOD AND SYSTEM UTILIZING PATTERN RECOGNITION FOR DETECTING ATYPICAL MOVEMENTS DURING PHYSICAL ACTIVITY

(71) Applicant: UTI Limited Partnership, Calgary (CA)

(72) Inventors: Ronald Reed Ferber, Calgary (CA); Dylan Robert John Kobsar, Vancouver (CA); Sean Thomas Osis, Cochrane (CA); Christian Arthur Clermont, Calgary (CA); Lauren Christine Benson, Calgary (CA)

(73) Assignee: UTI Limited Partnership, Alberta (CA)

( * ) Notice: Subject to any disclaimer, the term of this patent is extended or adjusted under 35 U.S.C. 154(b) by 630 days.

(21) Appl. No.: 16/764,648

(22) PCT Filed: Nov. 14, 2018

(86) PCT No.: PCT/CA2018/051442
§ 371 (c)(1),
(2) Date: May 15, 2020

(87) PCT Pub. No.: WO2019/095055
PCT Pub. Date: May 23, 2019

(65) Prior Publication Data
US 2021/0369143 A1 Dec. 2, 2021

Related U.S. Application Data

(60) Provisional application No. 62/586,565, filed on Nov. 15, 2017.

(51) Int. Cl.
*A61B 5/11* (2006.01)
*A61B 5/00* (2006.01)
(Continued)

(52) U.S. Cl.
CPC ............. *A61B 5/1118* (2013.01); *A61B 5/112* (2013.01); *A61B 5/6801* (2013.01); *G06N 20/00* (2019.01);
(Continued)

(58) Field of Classification Search
CPC ..... A61B 5/112; A61B 5/1123; A61B 5/7246; A61B 5/7275
See application file for complete search history.

(56) References Cited

U.S. PATENT DOCUMENTS 8,821,417 B2    9/2014  McGregor et al.
11,016,111 B1 * 5/2021  Chuang ................ A61B 5/6807
(Continued)

FOREIGN PATENT DOCUMENTS

WO    2015079436 A1    6/2015

OTHER PUBLICATIONS

Abstract—Kobsar et al—"Using Wearable Technology to Identify Abnormal Strides Within a Single Runner", Calgary, Canada, International Calgary Running Symposium, Aug. 14, 2014.
(Continued)

*Primary Examiner* — Lawrence S Galka
(74) *Attorney, Agent, or Firm* — Taft Stettinius & Hollister LLP

(57) ABSTRACT

Methods, systems and devices are provided for utilizing user movement data obtained from one or more wearable sensors during physical activity to compare individualized changes overtime, for example typical versus atypical movement patterns, with subgroup analyses for assessing changes between other users in order to develop an assessment of movement for, for example, tracking injury risk, performance, and/or rehabilitation. The movement information may comprise multi-sensor, high dimensional datasets. Techniques are provided for integrating human movement
(Continued)

data from one or more wearable sensor with one or more additional data sources to define an individualized movement profile of a user's movements. The user or another individual may be notified when the user's movements deviate from this individualized movement profile.

17 Claims, 15 Drawing Sheets

(51) Int. Cl.
*G06N 3/08* (2023.01)
*G06N 20/00* (2019.01)
*G06N 20/10* (2019.01)
*G16H 20/30* (2018.01)

(52) U.S. Cl.
CPC ...... *G16H 20/30* (2018.01); *A61B 2560/0242* (2013.01); *A61B 2562/04* (2013.01)

(56) References Cited

U.S. PATENT DOCUMENTS

| | | | |
|---|---|---|---|
| 2006/0025229 A1* | 2/2006 | Mahajan | A63B 24/0003 473/131 |
| 2011/0190667 A1 | 8/2011 | Alwan et al. | |
| 2013/0110011 A1 | 5/2013 | McGregor et al. | |
| 2014/0303900 A1 | 10/2014 | Rahman et al. | |
| 2017/0039358 A1* | 2/2017 | Yuen | G06F 21/32 |
| 2019/0150793 A1* | 5/2019 | Barth | A61B 5/112 |

OTHER PUBLICATIONS

Poster—Kobsar et al—"Using Wearable Technology to Identify Abnormal Strides Within a Single Runner", Calgary, Canada, International Calgary Running Symposium, Aug. 14, 2014.
Cola et al—"An On-Node Processing Approach for Anomaly Detection in Gait", IEEE Sensors Journal, Nov. 2015.
Abstract—Clermont et al—"The Use of Wearable Technology to Monitor Subject-Specific Running Gait Patterns", Calgary, Canada, SPIN Summit, Nov. 17, 2016.
Poster—Clermont et al—"The Use of Wearable Technology to Monitor Subject-Specific Running Gait Patterns", Calgary, Canada, SPIN Summit, Nov. 17, 2016.
Abstract—Clermont et al—"The Use of a 3d Accelerometer to Quantify Subject-specific typical and 'atypical' Running Gait Patterns", Brisbane, Australia, 2017 International Society of Biomechanics, Jul. 23, 2017.
Poster—Clermont et al—"The Use of a 3d Accelerometer to Quantify Subject-specific typical and 'atypical' Running Gait Patterns", Brisbane, Australia, 2017 International Society of Biomechanics, Jul. 23, 2017.
Ahamed et al., "Using Wearable Sensors to Classify Subject-specific Running Biomechanical Gait Patterns Based on Changes in Environmental Weather Conditions," PLoS One, Sep. 2018, vol. 13 (9), pp. e0203839.

Benson et al., "Classifying Running Speed Conditions Using a Single Wearable Sensor: Optimal Segmentation and Feature Extraction Methods," Journal of Biomechanics, Apr. 2018, vol. 71, pp. 94-99.
Benson et al., "The Use of Wearable Devices for Walking and Running Gait Analysis Outside of the Lab: A Systematic Review," Gait Posture, Jun. 2018, vol. 63, pp. 124-138.
Clermont et al., "Classification of Higher- and Lower-Mileage Runners Based on Running Kinematics," Journal of Sport and Health Science, Aug. 2017, pp. 1-9.
Clermont et al., "The Use of Wearable Technology to Monitor Subject-Specific Running Gait Patterns," Conference: 11th Annual SPort INnovation (SPIN) Summit, At Calgary, Alberta, Canada, Nov. 2016, 2 pages.
Clermont et al., "The Use of a 3d Accelerometer to Quantify Subject-specific 'typical' and 'atypical' Running Gait Patterns", In proceeding of: International Society of Biomechanics Congress XXVI, 2017.
Cola et al., "An On-Node Processing Approach for Anomaly Detection in Gait", IEEE Sensors Journal, Nov. 2015, vol. 15(11), pp. 6640-6649.
Frederick et al., "Why Change Gaits? Dynamics of the Walk-Run Transition", Journal of Experimental Psychology Human Perception & Performance, Mar. 1995, vol. 21(1), pp. 183-202.
International Patent Application No. PCT/CA2018/051442, International Search Report and Written Opinion dated Jan. 24, 2019.
Kobsar et al., "Classification Accuracy of a Single Tri-Axial Accelerometer for Training Background and Experience Level in Runners", Journal of Biomechanics, Jul. 2014, vol. 47(10), pp. 2508-2511.
Kobsar et al., "Wearable Sensors to Predict Response to a Hip Strengthening Exercise Intervention in Patients With Knee Osteoarthritis", Journal of Neuro engineering and Rehabilitation, Apr. 2007, vol. 25(1), pp. S23-S24.
Kobsar et al., "Wearable Sensor Data to Track Subject-Specific Movement Patterns Related to Clinical OutcomesUsing a Machine Learning Approach," Sensors, Aug. 2018, vol. 18 (9), pp. E2828.
Kobsar et al., "Gait Biomechanics and Patient-Reported Function as Predictors of Response to a Hip Strengthening Exercise Intervention in Patients with Knee Osteoarthritis", Plos One, Oct. 2015, vol. 10(10), e0139923.
Lau et al., "Support Vector Machine for Classification of Walking Conditions of Persons After Stroke With Dropped Foot", Human Movement Science, Aug. 2009, vol. 28(4), pp. 504-514. https://doi.org/10.1016/j.humov.2008.12.003.
Mannini et al., "A Machine Learning Framework for Gait Classification Using Inertial Sensors: Application to Elderly, Post-Stroke and Huntington's Disease Patients," Sensors, Jan. 2016, vol. 16 (1), pp. 1-14.
Phinyomark et al., "Gender Differences in Gait Kinematics in Runners with Iliotibial Band Syndrome," Scandinavian Journal of Medicine and Science in Sports, Dec. 2015, vol. 25 (6), pp. 744-753.
Tao et al., "Gait Analysis Using Wearable Sensors", Sensors (Basel, Switzerland), Feb. 2012, vol. 12(2), pp. 2255-2283.
Yang et al., "A Machine Learning Approach to Assessing Gait Patterns for Complex Regional Pain Syndrome", Medical Engineering & Physics, Jul. 2012, vol. 34(6), pp. 740-746.

* cited by examiner

METHOD AND SYSTEM UTILIZING PATTERN RECOGNITION FOR DETECTING ATYPICAL MOVEMENTS DURING PHYSICAL ACTIVITY

CROSS-REFERENCE TO RELATED APPLICATIONS

This application is a U.S. National Phase of International PCT Application No. PCT/CA2018/051442 filed on Nov. 14, 2018, which claims benefit of U.S. Provisional Patent Application No. 62/586,565 filed Nov. 15, 2017, each of which are incorporated herein by reference in their entirety.

FIELD

The present disclosure relates generally to methods, systems and devices for detecting deviations in the movements of an individual during physical activity.

BACKGROUND

Wearable sensor technology is a rapidly growing industry with many applications in the fitness, sport, and healthcare industries. While most commercial applications of wearable sensors in this industry are for tracking the quantity of movement of a user, for example distance traveled, they generally provide little or no information on the quality of the movement of the user.

In particular, existing approaches have not provided a useful and effective way of tracking the movement of an individual in a classification subspace, meaning between subgroups of user data, over time. Some existing approaches do not use wearable sensors but instead rely on image based and other types of sensors. These approaches are difficult to utilize outside of the lab.

Further, some existing approaches examine a gait pattern of a person on average, but do not consider individual movement segments, for example a gait cycle. Also, some existing approaches that attempt to detect atypical movement patterns only use a single motion sensing device and therefore are only able to use data from a single sensor.

Other existing approaches attempt to obtain multivariate threshold parameters for assessing typical and atypical movement patterns but are unable to do so outside of the lab. Additionally, existing approaches fail to combine an assessment of within-subject movement deviations with the sub-grouping of movement patterns between individuals.

Improvements in wearable sensor technology relating to sensing and tracking the quality of user movements are therefore desirable.

The above information is presented as background information only to assist with an understanding of the present disclosure. No assertion or admission is made as to whether any of the above might be applicable as prior art with regard to the present disclosure.

SUMMARY

According to an aspect, the present disclosure is directed to a device comprising: at least one computer processor; computer memory in communication with the at least one computer processor and for storing computer executable instructions, which when executed by the at least one computer processor cause the at least one computer processor to perform operations comprising: receive individualized movement profile information for a user, wherein the individualized movement profile information defines a subspace in which movements of the user are considered typical for the user; receive new movement information of the user relating to a physical activity from one or more wearable motion sensors; determine if the movements of the user during the physical activity are typical for the user by determining if the movements according to the new movement information are located within the subspace; generate, in response to determining that the movements of the user during the physical activity are typical for the user, a first output indication signal; identify, in response to determining that the movements of the user during the physical activity are not typical for the user, a subgroup from among a plurality of subgroups that most closely corresponds to the new movement information, wherein each subgroup consist of movement information of users all sharing on one or more predetermined characteristics, wherein each subgroup defines a subspace associated with the one or more predetermined characteristics of the users of the subgroup such that the movements of the of the users of the subgroup according to the movement information are located within the subspace of the subgroup; determine if the identified subgroup is the same or different as a predefined subgroup associated with the user; generate, in response to determining that the identified subgroup is the same as the predefined subgroup, a second output indication signal; and generate, in response to determining that the identified subgroup is different than the predefined subgroup, a third output indication signal.

In an embodiment, the subspace of the subgroup comprises a multivariate threshold boundary such that the movements of the users of the subgroup according to the movement information are located within the multivariate threshold boundary of the subgroup.

In an embodiment, the subspace of the individualized movement profile is a multivariate subspace, wherein the individualized movement profile information comprises a multivariate threshold boundary defining an area or region of the multivariate subspace, and wherein the determining if the movements according to the new movement information are located within the subspace involves determining if the user movements are located within the multivariate threshold boundary.

In an embodiment, the identifying a subgroup from among the plurality of subgroups involves comparing the new movement information to movement information of users of at least some of the plurality of subgroups using a supervised machine learning process.

In an embodiment, the movement information of users of a subgroup comprises a plurality of values where each of at least some of the values is an average of movement segments of a particular user of the subgroup.

In an embodiment, the device is configured to generate or modify the individualized movement profile information for the user by receiving movement data representing a plurality of individual movement segments of the user from one or more wearable motion sensors, and using an unsupervised machine learning process on the received movement data to define an expected multivariate range of movement values for the user.

In an embodiment, the device is configured such that the unsupervised machine learning process generates a model based on the received movement data describing values and multivariate relationships to be considered typical for the received movement data, and the unsupervised machine learning process then defines the subspace in which movements of the user are considered typical based on the generated model.

In an embodiment, the device is configured to amalgamate the new movement information into the individualized movement profile information of the user in response to determining that the movements of the user during the physical activity are typical for the user, and saving the amalgamated individualized movement profile information in the memory.

In an embodiment, the individualized movement profile information for the user corresponds to external condition information for providing context to the individualized movement profile of the user.

In an embodiment, the external condition information comprises information relating to at least one of terrain, route, weather, season, or time of day.

In an embodiment, the device is configured to receive new external condition information associated with the new movement information, and wherein at least one of the determining if the movements of the user during the physical activity are typical for the user, and the identifying a subgroup from among the plurality of subgroups that most closely corresponds to the new movement information is based on the received new external condition information.

According to an aspect, the present disclosure is directed to a method comprising: receiving, by at least one computer processor, individualized movement profile information for a user from a database, wherein the individualized movement profile information defines a subspace in which movements of the user are considered typical for the user; receiving, by at least one computer processor, new movement information of the user relating to a physical activity from one or more wearable motion sensors; determining, by at least one computer processor, if the movements of the user during the physical activity are typical for the user by determining if the movements are located within the subspace; generating, by at least one computer processor, in response to determining that the movements of the user during the physical activity are typical for the user, a first output indication signal; identifying, by at least one computer processor, in response to determining that the movements of the user during the physical activity are not typical for the user, a subgroup from among a plurality of subgroups that most closely corresponds to the new movement information, wherein each subgroup consist of movement information of users all sharing on one or more predetermined characteristics, wherein each subgroup defines a subspace associated with the one or more predetermined characteristics of the users of the subgroup such that such that the movements of the of the users of the subgroup according to the movement information are located within the subspace of the subgroup; determining, by at least one computer processor, if the identified subgroup is the same or different as a predefined subgroup associated with the user; generating, by at least one computer processor, in response to determining that the identified subgroup is the same as the predefined subgroup, a second output indication signal; generating, by at least one computer processor, in response to determining that the identified subgroup is different than the predefined subgroup, a third output indication signal.

According to an aspect, the present disclosure is directed to a non-transitory computer-readable storage medium storing instructions that when executed by at least one computer cause the computer to perform operations comprising operations according to the method set forth in the previous paragraph.

According to an aspect, the present disclosure is directed to a device comprising: one or more computer processors; computer memory in communication with the one or more processors and for storing computer executable instructions, which when executed by the one or more processors cause the one or more processors to perform operations comprising: receive a target subgroup indication for a user, wherein the target subgroup is among a plurality of subgroups, wherein each subgroup consist of movement information of users all sharing on one or more predetermined characteristics, wherein each subgroup defines a subspace associated with the one or more predetermined characteristics of the users of the subgroup such that the movements of the of the users of the subgroup according to the movement information are located within the subspace of the subgroup; receive first movement information of the user relating to a physical activity from one or more wearable motion sensors; receive second movement information of the user relating to the physical activity from one or more wearable motion sensors, where the second movement information is sensed from the user later in time relative to the first movement information; determine if the second movement information more closely or less closely corresponds to the movement information of the users of the target subgroup compared to the first movement information; generate, in response to determining that the second movement information more closely corresponds, a first output indication signal; generate, in response to determining that the second movement information less closely corresponds, a second output indication signal.

The foregoing summary provides some aspects and features according to the present disclosure but is not intended to be limiting. Other aspects and features of the present disclosure will become apparent to those ordinarily skilled in the art upon review of the following description of specific embodiments in conjunction with the accompanying figures. Accordingly, the drawings and detailed description are to be regarded as illustrative in nature and not restrictive.

BRIEF DESCRIPTION OF THE DRAWINGS

Embodiments of the present disclosure will now be described, by way of example only, with reference to the attached Figures.

DETAILED DESCRIPTION

Figure 1:
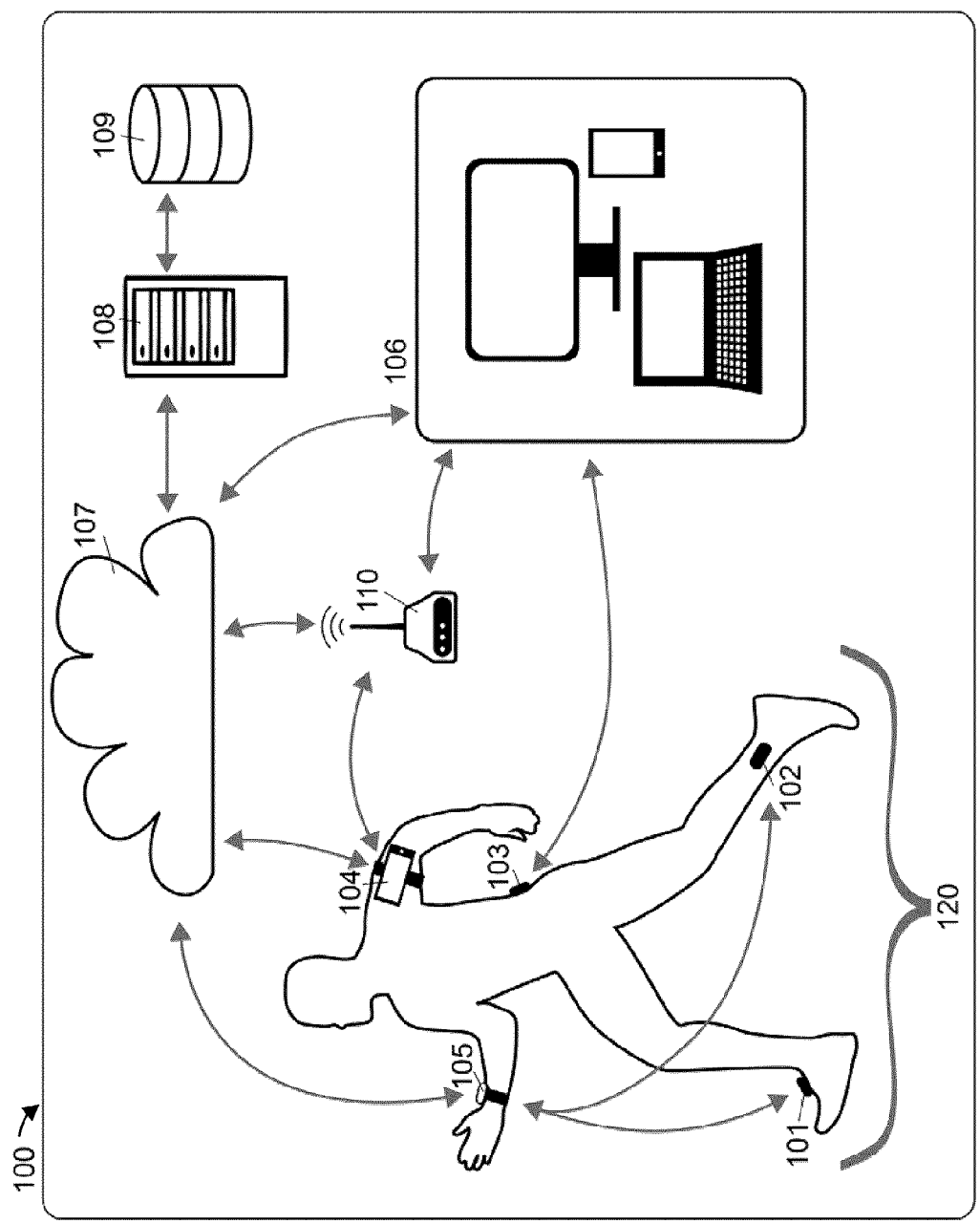
FIG. 1 is a representation of a system according to the present disclosure comprising wearable sensors and other computing devices.

Wearable sensor technology has the potential to measure subtle changes in human movement patterns and provide actionable insights for injury prevention and detection, training, and rehabilitation decisions of users, clinicians, and other health professionals.

The present disclosure generally relates to improvements in wearable sensor technology, and more specifically to improvements in wearable sensor technology devices, systems, and methods. The improvements to this technology include improvements to the functioning of electronic devices and systems to provide more useful and effective sensing and tracking/measuring capabilities.

In an aspect, the present disclosure is directed to methods, systems and devices for utilizing user movement data obtained from one or more wearable sensors to compare individualized changes overtime, for example typical versus atypical movement patterns, with subgroup analyses for assessing changes between other users in order to develop an assessment of movement for, for example, tracking injury risk, performance, and/or rehabilitation. The movement information may comprise multi-sensor, high dimensional datasets.

In an aspect, the present disclosure is directed to techniques for integrating human movement data from one or more wearable sensors with one or more additional data sources to define an individualized movement profile of a user's movements, hereafter referred to as a movement patterns. The movements may be movements from any activity, such as walking, running, cycling, swimming, jumping, or other repetitive movement task. The user or another individual may be notified when the user's movements deviate from this individualized movement profile. One or more deviation thresholds may be used when assessing deviations in a user's movements. Wearable sensor data used for this pattern recognition may include data from one or more types of sensors including but not limited to accelerometers, gyroscopes, magnetometers, global positioning systems, galvanic skin response sensor, and heart rate monitors.

The present techniques include linear and non-linear pattern recognition algorithms that may utilize the user movement data to identify and track out of lab changes over time within an individual that may be related to one or more of injury risk, performance, or rehabilitation progress. The present techniques may also integrate changes in conditions or external factors, for example the running/walking/cycling speed of the activity or user (e.g. running speed, walking speed, cycling speed, etc.), weather, terrain, and route, and subgroup comparisons, for example male versus female, injured versus non-injured, competitive versus recreational, experienced versus inexperienced, etc., to provide additional context to any movement patterns and/or movement deviations. Specifically, the outcomes of the present techniques may provide users or others with information regarding if and how user's movement patterns are deviating from their individualized movement profile. This information may be used for making adjustments to training or rehabilitation.

FIG. 1 is a representation of a system 100 according to the present disclosure comprising wearable sensors and other computing devices. System 100 comprises a user sensor network 120, one or more personal computing devices 106 such as a personal computer, a notebook computer, and a tablet, a communication and/or processing network 107, a server 108, a database 109, and a wireless access point 110, for example a cellular base station, Wi-Fi station, satellite, etc. Various arrows represent example communication paths between the entities in FIG. 1, which may be wireless or wired communication links. However, other communication paths are also possible, thus the arrows of FIG. 1 are not meant to be limiting.

Data relating to the movement of a user, referred to herein as movement information, may be detected, sensed and/or measured using one or more wearable motion sensors positioned on or about the user. FIG. 1 illustrates an example sensor network 120 comprising sensors 101-105 that may be used to the collect the user movement information or other user information that may then be used to create an individualized movement profile. Sensor devices 101-105 shown in FIG. 1 may be standalone sensors or they may form part of other devices, for example a smart phone, a smart watch, a tablet, smart glasses, or any other suitable device. The other devices may include more processing power and/or computer functionality compared to mere sensor devices. The individualized movement profile may be a gait profile or any other suitable type of movement profile.

The example sensor network 120 includes two distal sensors, 101 and 102, which are positioned at the lower legs or ankles of the user. Network 120 further includes a sensor 103 positioned in the lower back region, a sensor 104 positioned on the arm, which may be a sensor in a smart phone, and a sensor 105 positioned at the wrist, which may be a sensor in a smart watch. Sensor network 120 may be a wireless personal area network, a body area network, or an IEEE 802.15.6 standard compliant network.

The one or more sensors according to the present disclosure may be any device that has the capability to sense or measure bodily movement, such as but not limited to 3D accelerometers, 3D gyroscopes, magnetometers, Global Positioning Systems, etc. In addition, sensor network 120 may comprise one or more devices that have the capability to sense or measure physiological responses, such as but not limited to heart rate, galvanic skin response, etc. The present disclosure is not limited to any specific sensor network configuration. In other words, the number and type of sensors and their placement may vary as long as there is at least one sensor with the ability to measure the motion of the body of the user.

In at least some embodiments, minimum specifications for wearable motion sensors include one or more of an accelerometer with ±2 G-forces at 100 Hz, a gyroscope with ±250 degrees per second at 100 Hz, and a magnetometer ±1.3 gauss at 100 Hz. While these specifications may be the minimum specifications in certain applications, different ranges may be more effective depending on the placement of sensors and/or the type of physical activity. For example, sensors located on the shank or foot during running may require greater accelerometer range (e.g., ±16 G-forces) given the potential for large impact accelerations.

The flow of data between sensors, and including any processing devices, may vary depending on the number or type of sensors and their processing capabilities in the sensor network. For example, in sensor network 120 of FIG. 1, wearable sensors 101, 102, and 103, may have only limited processing power, for example for performing basic preprocessing analyses. Such sensors may therefore be communicatively coupled (i.e., streaming during data collection or uploading stored data post collection) to another device having additional processing capabilities for, for example, processing, analyzing, or outputting information to the user. Additionally, or alternatively, the other devices may have enhanced communication capabilities, such as cellular, Wi-Fi, or other communication capabilities relative to simple sensor devices for communicating sensor data (e.g. more quickly, more effectively, more securely, over longer transmission distances, etc.). Further, some wearable smart devices, such as smart phones and smart watches, etc., have the capability to measure bodily motion and/or physiological responses, in addition to having sufficient processing power for analyzing data or connecting to external networks or devices.

The processing of data according to the present disclosure may be centralized at one device, whether worn by the user or located remotely from the user, or the processing may be distributed among two or more processing devices. Example devices that may perform processing operations in the system of FIG. 1 include smart phone 104, smart watch 105, personal computer, notebook computer, tablet 106, and server 108.

A few examples of data flow between devices are now described. The data flow between devices may occur either during or following a data collection session. A data collection session is a time period or periods during which sensor data is collected during a physical activity. In a first example, sensor data from sensors 101 and 102 is communicated to smart watch 105, and from smart watch 105 to an external network 107. The data may be communicated to external network via wireless access point 110. The data may be communicated over network 107 to a computing device 106 or to server 108. The data communicated to network 107 may include sensor data generated at smart watch 105. The sensor data may be communicated in real-time during the physical activity of the user, or may be communicated at a later time(s) whether periodically, intermittently or all at once, and involves data collected from all three sensors.

In a second example, sensor data from lower back sensor 103 is communicated to smart phone 104. Smart phone 104 itself may generate sensor data. The real time or post collection processing or analyses of data may be performed at smart phone 104.

In a third example, lower back sensor 103 generates and stores sensor data. The sensor data may then be uploaded to computer for analysis following the data collection.

The data sent from sensors or other devices may be raw data, or it may be compressed and/or formatted in any suitable way. The data may be encoded for security reasons, for forward error correction, or for any other suitable reason. In some embodiments, the data may be encrypted.

These three examples represent but a few embodiments. Sensor networks and data flow processes may incorporate any suitable combinations of such sensors, as well as data storage, data transfer, or live streaming techniques.

Given the cyclical nature of human movement patterns such as walking, cycling, running, swimming, etc., user movement data may be collected continuously over an entire physical activity episode (e.g. a workout session) or part thereof, but broken down into a number of individual movement segments for analysis. In this manner, each movement segment may be identified as an individual observation of a repeatable or cyclical movement, for example gait cycle, swimming stroke, cycling stroke, jump, etc., of which a multitude of discrete and continuous variables may be measured.

For example, where the physical activity is running, sensor data may be used to generate discrete variables that describe the overall spatial (e.g., step length, stride length, vertical displacement of the center of mass, etc.) and/or temporal (e.g., step time, stride time, ground contact time, flight time, etc.) parameters of an individual gait cycle. Additional discrete variables, for example peak impact accelerations, peak angular velocities, root mean square of linear accelerations, asymmetry of spatial and temporal parameters, may further describe the 3D movement at various locations of the body.

Moreover, the use of more complex measures, which relate to the overall pattern of movement itself, may be generated utilizing the time-series data from one or more motion sensor devices (e.g., accelerometer, gyroscope, magnetometer, etc.). For example, a 3D linear acceleration signal recorded over a movement segment may be used as a set of variables to describe the motion of that repeatable event. This data may be time normalized to create an equal number of time-series points (e.g., 0-100%), thereby simplifying comparisons between movement segments. Additionally, these time-series data may be reduced to a limited number of components that describe the overall pattern of motion using a principal component analysis. Therefore, by providing even a single sensor to the user that contains one or more motion sensing components (e.g., accelerometer, gyroscope, magnetometer, etc.), it is possible to generate multiple variables, and in some embodiments many variables, to describe each movement segment. However, by utilizing multiple wearable sensors, hundreds or even thousands of variables may be generated to describe a single movement segment in a high dimensional variable space. Further, by collecting this data continuously over an entire physical activity episode or multiple episodes, this high dimensional set of data may be repeated over thousands of individual movement segments and used to define a user's individualized movement profile.

According to the present disclosure, an individualized movement profile of a user may be generated by integrating the sensor data describing multiple (e.g. thousands) individual movement segments with machine learning techniques. Regardless of whether the data describing each movement segment consists of a limited number of simple, discrete measures, or a large number of complex variables, an unsupervised machine learning algorithm may utilize these data collected over many individual movement segments to define an expected multivariate range of values for the user, as will be described further below. The multivariate range of values defines a subspace in which movements of the user are considered typical for the user.

Figure 2A:
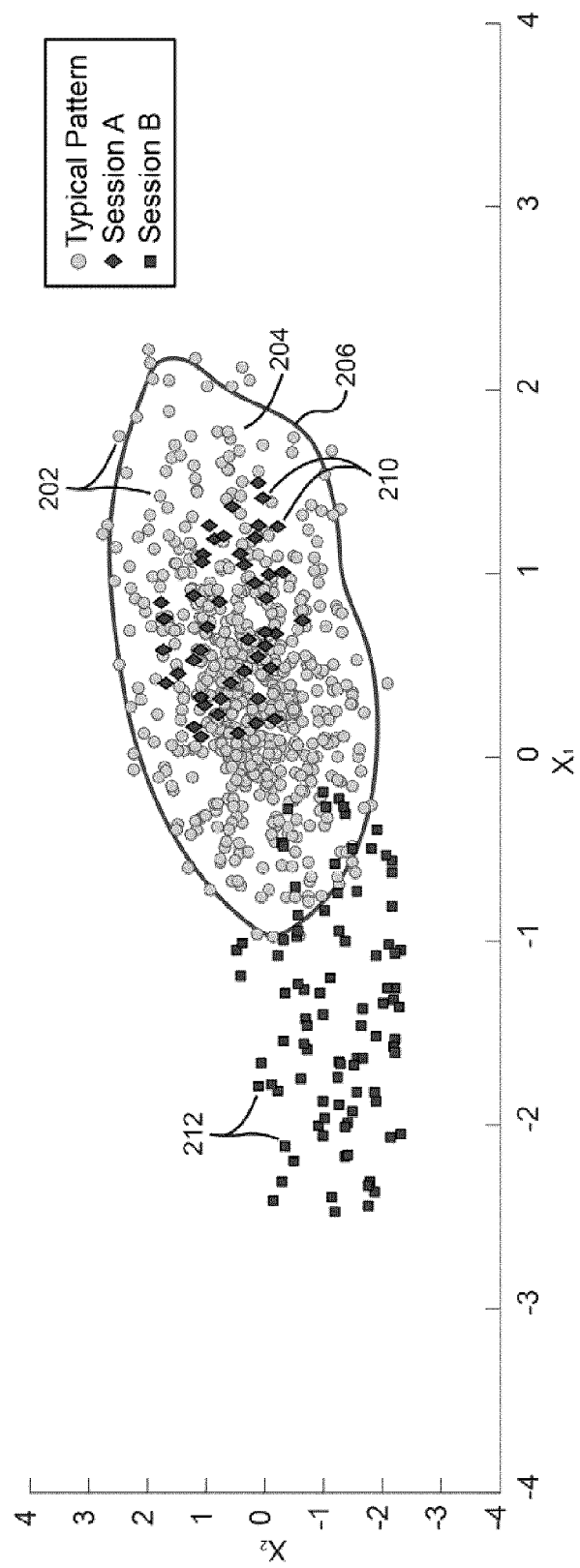
FIG. 2A is a graph of an example two-dimensional subspace consisting of two variables collected with a wearable motion sensor on a user.

FIG. 2A is a graph of an example two-dimensional subspace consisting of two variables ($X_1$ and $X_2$) collected with a wearable motion sensor on a user. Each variable may represent any suitable movement variable generated from an acceleration signal, angular velocity signal, etc. Each point on the graph represents an individual movement segment of the user. Again, a movement segment may be a movement cycle, such as a gait cycle, swim stoke, etc. FIG. 2A presents a simple illustration of data from thousands of typical movement segments of the user, depicted by the light grey circles 202, which are used to define an individualized movement profile for the user. The individualized movement profile information may define a subspace in which movements of the user are considered typical for the user. In the example of FIG. 2A, the subspace 204 is defined by boundary 206. The subspace of the individualized movement profile may be a multivariate subspace, where the individualized movement profile information comprises a multivariate threshold boundary defining an area or region of the multivariate subspace.

It is important to note that FIG. 2A is presented for visualization purposes only and as such only two variables are presented. As previously outlined, one or more sensors may be used to generate hundreds or even thousands of variables that describe each movement segment. Such a high dimensional subspace would not be able to be represented in a simple two-dimensional figure.

In this example of FIG. 2A, the individualized movement profile is associated with a set of conditions and/or external factors, hereinafter referred to as external conditions for simplicity. In some embodiments, the individualized movement profile of a user refers to a user's typical movement pattern under a specific set of one or more external conditions. Thus, these embodiments do not utilize a singularly defined typical movement pattern boundary across varying external conditions such as, but not limited to, terrain, route, speed, weather, season, time of day, warm-up status, footwear, braces, or orthotics. In other words, the individualized movement profile of a user may contain multiple typical movement pattern boundaries that are uniquely defined for different sets of external condition(s) (e.g. tasks, routes, speeds, etc.), and may be continually analyzed and followed over time.

Figure 2B:
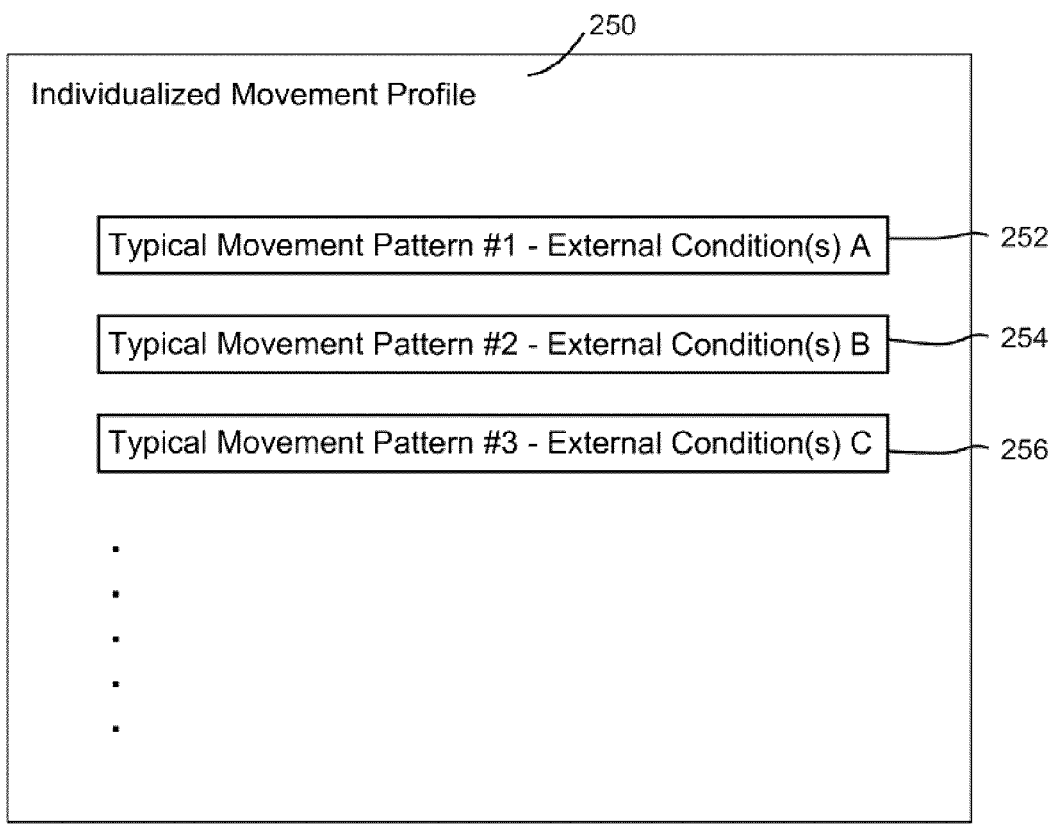
FIG. 2B represents the content of an example individualized movement profile for a user.

FIG. 2B represents the content of an example individualized movement profile 250 for a user. Individualized movement profile 250 may comprise one or more typical movement patterns 252, 254, 256 for the user, each associated with a unique set of external conditions. As an example, the first typical movement pattern 252 may correspond to "season=summer", and "terrain=flat". Second typical movement pattern 254 may correspond to "season=summer", and "terrain=moderately hilly". Third typical movement pattern 256 may correspond to "season=winter", and "weather=snowing". Individualized movement profile 250 may be stored in a computer readable medium as a data structure or in any other suitable way.

Defining the boundary or boundaries of the typical data, for example boundary 206 in FIG. 2A, may be accomplished with a linear, or non-linear (as shown in FIG. 2A), unsupervised machine learning algorithm. The unsupervised machine learning algorithm may be any suitable algorithm, including, but not limited to, one-class support vector machine, principal component analysis, or multivariate Gaussian distribution. For these unsupervised algorithms, sensor data may be organized as a set of wearable sensor variables that are collected over a large number of movement segments, for example, 500 or more movement segments, based on a repetitive movement such as running or cycling. These data may be organized in a matrix or other suitable data structure or format that contains a number of wearable sensor variables and the many individual movement segments (for example hundreds or thousands) collected from each sensor. A matrix may have the size: variables×movement segments.

In one embodiment using standard machine learning techniques such as a one-class support vector machine, movement sensor data is organized in the abovementioned variable by movement segment manner and a linear or non-linear hypersphere, meaning a sphere that is greater than 3-dimensions in size and shape, is calculated to determine the boundary of typical movement. This boundary is created by identifying the support vectors, for example movement segment observations in the subspace, that define the most extreme (meaning furthest from the average) multivariate combinations of sensor data that are determined to be typical movement segments, thereby defining the boundary or threshold at which movement segments outside will be defined atypical. In at least some embodiments, the sensor data used to define these boundaries or thresholds of typical movement patterns comes from a minimum of two data collection sessions. By obtaining two or more data collection sessions, containing many movement segments, the support vectors and typical boundary that are obtained will typically remain robust to normal, minor day to day variations in the data. Further adjustments to the sensitivity of the boundary can be accomplished by adjusting standard unsupervised machine learning parameters related to outlier control and may be visualized as the potential non-linear change in the volume of the subspace defined by the boundary line 206 in FIG. 2A.

The parameter(s) for outlier control may be determined based on the user selecting their preferred level of outlier sensitivity preference. The user may define their sensitivity as either: "high", "moderate", or "low", other similar ordinal scales, or percentage of outliers in training data (i.e., percentage of data points 202 outside of boundary threshold 206). These settings relate to how tight, or well-defined the boundary will be and will thereby influence the likelihood of identifying atypical movement segments in new data collection sessions. For example, selecting a "high" sensitivity setting will lead to a tighter boundary and, for example, a regularization parameter in a one-class support vector machine (e.g., Nu parameter) to be set to a value of 0.05. On the other hand, selecting a "low" sensitivity setting will lead to a wider boundary and, for example, a regularization parameter in a one-class support vector machine (e.g., Nu parameter) to be set to a value of 0.50. In FIG. 2A, the multivariate threshold boundary 206 defines the area of the two-dimensional subspace that the user's movement segments would be considered typical. In an embodiment, the movement segments may be considered typical under comparable external conditions (e.g. speed, weather, season, time of day, warm-up status, footwear, braces, or orthotics).

Although FIG. 2A demonstrates a two-dimensional subspace, the present disclosure contemplates the integration of multiple sources of data from multiple sensors (e.g., accelerometers, gyroscopes, magnetometers, etc.), thereby utilizing a high-dimensional subspace to define the user's typical movement pattern for one or more specific external conditions.

In addition to defining an individualized movement profile of a user, new sensor data obtained during a subsequent physical activity may be compared to the user's previously defined individualized movement profile. For example, FIG. 2A illustrates two additional data collection sessions, Session A and Session B, which may be compared to the individualized movement profile of the user. The data points of Session A, depicted by the dark grey diamonds 210, fall within the boundary 206 of the individualized movement profile. Thus the movement data of Session A is deemed a data collection that is within the typical movement pattern for this user.

However, the majority of the data points of Session B, depicted by dark grey squares 212, fall outside of boundary 206 of the individualized movement profile. Therefore, the movement data of Session B would be deemed a data collection session is not within the typical movement pattern for this user. Thus, the movement data of Session B could be considered atypical.

As previously discussed, the individualized movement profile of a user may comprise two or more movement profiles each associated with a specific set of one or more external conditions. In some embodiments, the determination of whether the movement data is deemed a data collection session that is within or outside of the typical movement pattern for the user is based on the new movement data being associated one or more of the same external conditions as the data on which the individualized movement profile was established. Therefore, while the data of Session B in FIG. 2A may appear to be an atypical movement pattern for the user, if these external conditions are different than those under which the individualized movement profile was defined, then the data of Session B may not necessarily be deemed an atypical movement pattern.

In some embodiments, a more in-depth analysis may be performed on the movement data obtained during a collection session. For instance, individual sections of a data collection session may be identified as typical or atypical for the user. For example, a session may be divided into smaller sections, arranged chronologically, that each still contain many individual movement segments. For example, a data collection session may be divided into 5-minute sections, with each section containing all of the movement segments recorded during each time period. Having broken a session into multiple sections, each section of data may be compared to the user's previously defined individualized movement profile. If the movement data is located within the subspace of the individualized movement profile, meaning that the movement information is within the boundary, that particular section of data may be considered typical for the user. However, if a predefined percentage, for example a majority, of the movement data in the section is located outside of the subspace, meaning outside of the boundary, that particular section of data may be considered atypical for the user. Any suitable predefined percentage may be used in the assessment.

Therefore, collected sensor data may be subdivided into smaller sections, possibly of varying sizes, that may vary in their likeness of the typical movement pattern (i.e., typical or atypical). This segmentation may allow for a more direct analysis of how the movement patterns of a user change, not just over multiple data collection sessions, but throughout the duration of a single session. While this within-session analysis may be performed after the activity, it may also be performed in real-time or near real-time to provide immediate feedback to the user during the activity.

Injury Risk Tracking

Figure 3:
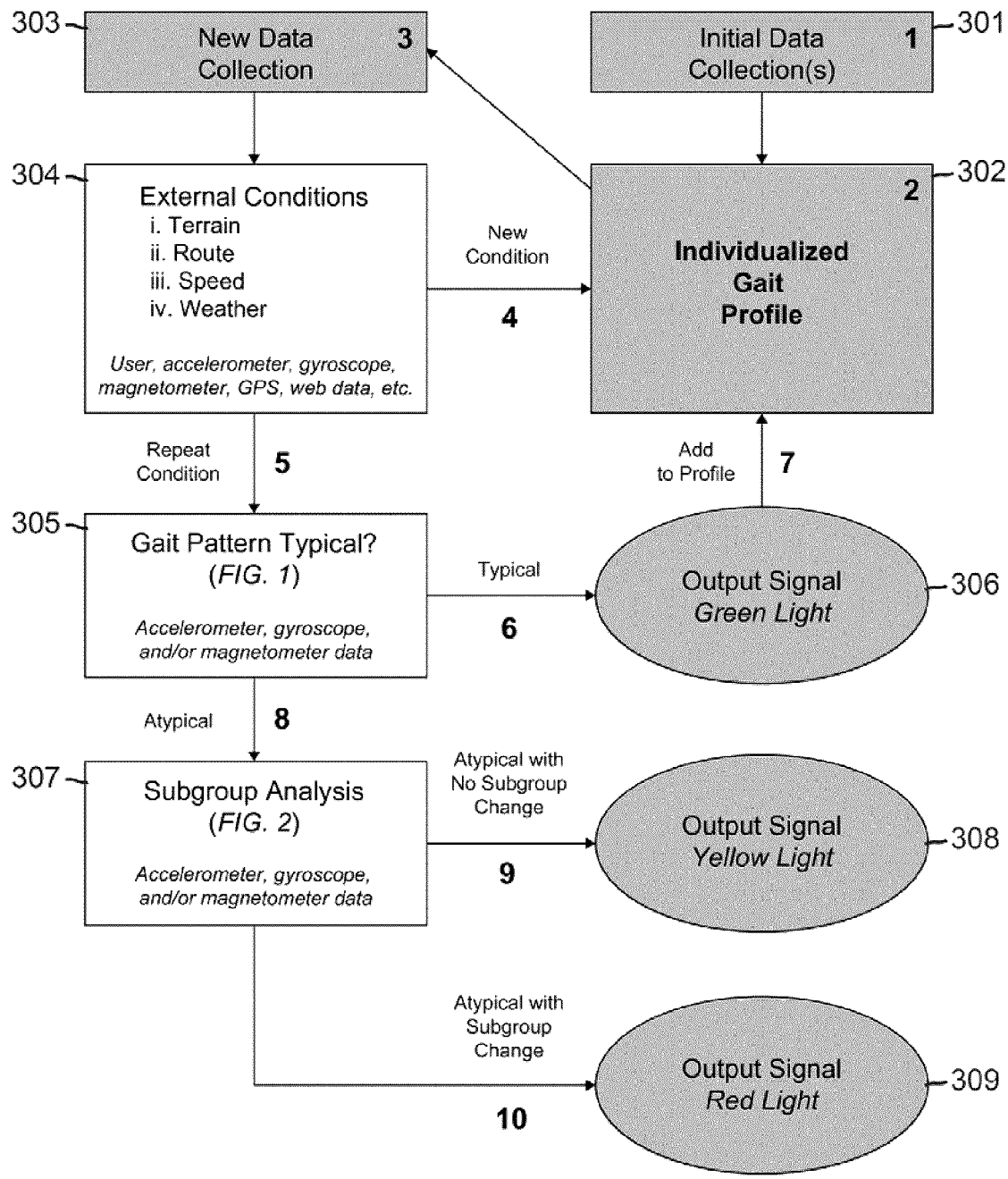
FIG. 3 is a process flow diagram of an example injury risk tracking method according to the present disclosure.

FIG. 3 is a process flow diagram of an example injury risk tracking method according to the present disclosure. Methods for processing sensor data to assess deviations in the movement data of a user are provided. In an embodiment, the method identifies deviations in new movement data of a user relative to the user's individualized movement profile.

In an embodiment, the method identifies deviations in new movement data of a user relative to movement data gathered from other users and organized into one or more subgroups.

In an embodiment, the movement pattern recognition techniques of the present disclosure are used for assessing and/or interpreting movement pattern deviations over time, for example within a single data collection session or over multiple days, weeks, months, etc., in a user's individualized movement profile. This information may be used to identify when the user is potentially injured and/or situations when the user's movements start to deviate and thus present a potentially increased risk for injury. Embodiments directed to these aspects are referred to herein as Injury Risk Tracking embodiments.

The process of FIG. 3 begins at block 301 with two or more initial data collection sessions where movement data from one or more motion sensors of the user is collected for the purpose of defining an individualized movement profile. However, in some other embodiments, only a single data collection session may be used to define an individualized movement profile.

The process proceeds to block 302 to define a user's set of typical movement pattern data within their individualized movement profile.

The process then proceeds to block 303 where new movement data may be collected for a user performing a physical activity.

The process, in some embodiments, then proceeds to block 304 where any external conditions associated with the new movement data are evaluated. The conditions may be evaluated using input from additional one or more data sources, for example from user input, accelerometers, gyroscopes, magnetometers, global positioning systems, or web data, to determine if the new data was collected under a "new condition", meaning a new set of external conditions, or under a "repeat condition" meaning a repeat set of similar external conditions. New data collected under a "new condition" means that the user's individualized movement profile does not contain a movement pattern for the specific set of conditions associated with the new data. A repeat condition means the user's individualized movement profile includes a movement pattern for the external conditions associated with the new data.

If the new movement data is defined as a new condition, then the process, in some embodiments, adds the new movement data as a new typical movement pattern in the user's individualized movement profile, as indicated by arrow 4. However, if the new movement data is defined as a repeat condition, the process proceeds to block 305 where the new movement data may be compared to typical movement pattern data of similar external conditions in the user's individualized movement profile.

If the new movement data is located within the subspace in which user movements are considered typical, under similar external conditions, and therefore deemed typical, the process proceeds to block 306 where an output indication signal may be generated. The output indication signal may indicate or otherwise cause to be indicated that the user's movement pattern is typical. The output indication signal may cause a device to generate an output perceivable by the user, such as a visual indication, audible indication, tactile indication, etc. In an embodiment, the output indication may be in the form of a green light output indicating that the new movement data is considered typical for the user under the particular external conditions.

Further, the new movement data may be amalgamated into the user's individualized movement profile to improve the robustness of the profile with continued use.

If the new movement data is not considered typical for the user at block 305, the process proceeds to block 307 where the new movement data may be further assessed in a subgroup analysis to interpret the amount and/or direction of deviation in the new movement data.

In an embodiment, a subgroup is a homogenous, or similar group of users, and thereby the set of movement data for all of the subgroup of users, based on one or more predetermined characteristics such as, but not limited to, age, gender, weight, height, geographical region, ethnicity, medical condition, training background (e.g. experienced vs. inexperienced), training status (e.g., competitive vs. recreation), training goal (e.g., marathon vs. 5 km) and injury status. There would typically be, in at least some embodiments, a plurality of different subgroups where each subgroup consists of movement information of users all sharing on one or more predetermined characteristics. Effectively it is the one or more predetermined characteristics that define the subgroup. Each subgroup defines a subspace associated with the one or more predetermined characteristics such that the movement data of the users of the subgroup are located within the subspace of the subgroup.

Figure 4:
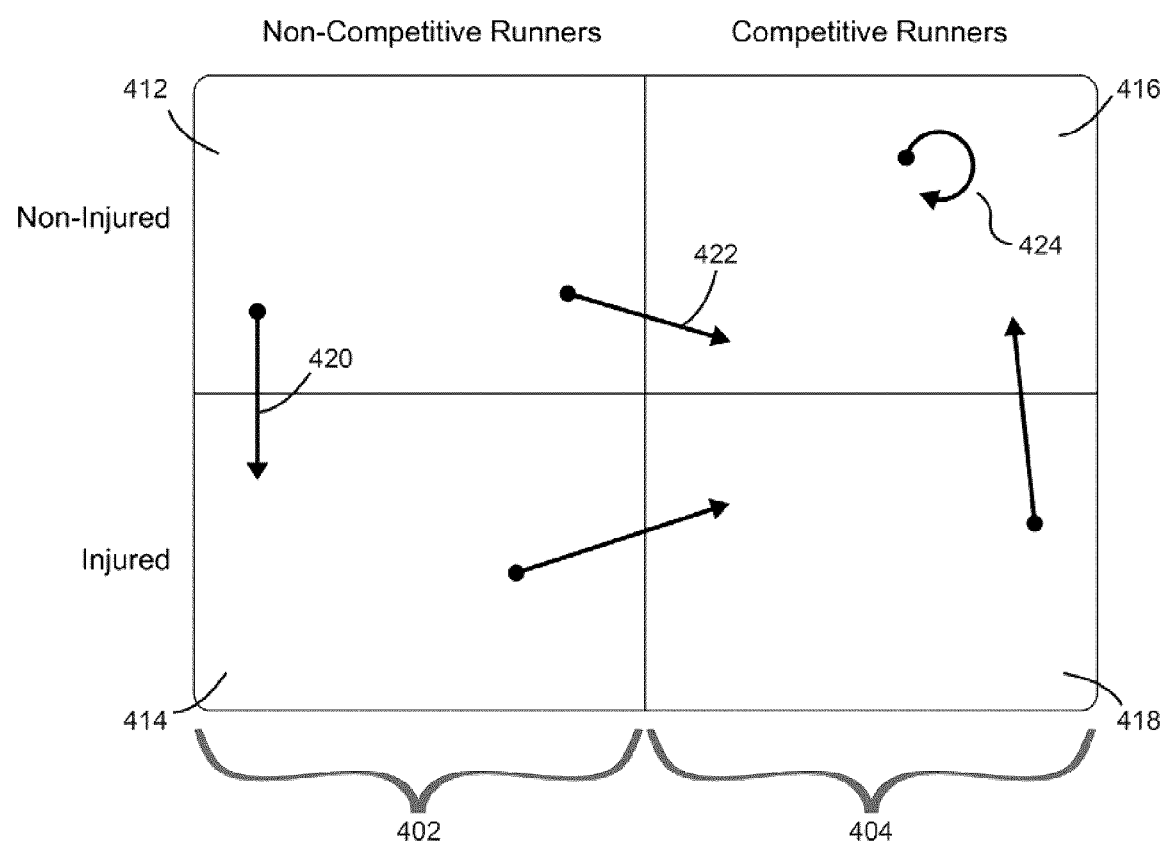
FIG. 4 is a diagram of a simple example set of subgroups to further explain the concept of subgroups.

FIG. 4 is a diagram of a simple example set of subgroups to further explain the concept of subgroups. An example set of subgroups may comprise a first subgroup 402 of non-competitive runners and a second subgroup 404 of competitive runners. The user movement data in each of these subgroups is associated by one predetermined characteristic, namely non-competitive versus competitive runner status. Another example set of subgroups comprises a first subgroup of non-injured, non-competitive runners 412, a second subgroup of injured, non-competitive runners 414, a third subgroup of non-injured, competitive runners 416, and a fourth subgroup of injured, competitive runners 418. The user movement data in each of these subgroups is associated by two predetermined characteristics, namely non-competitive versus competitive runner status and non-injured versus injured status.

FIG. 4 also includes arrows representing some example deviations in a user's movement data, for example compared to their individualized movement profile. For instance, new movement data collected from a non-injured, non-competitive runner may indicate the runner is trending towards, or is already in, an "injured" state (i.e. subgroup 414), as indicated by arrow 420. In another example, new movement data collected from a non-injured, non-competitive runner may indicate the runner is trending towards or is already in a "competitive" runner state (i.e. subgroup 416), as indicated by arrow 422. In a further example, new movement data collected from a non-injured, competitive runner may indicate the runner is remaining in the non-injured competitive runner state (i.e. subgroup 416), as indicated by arrow 424. The amount (i.e. magnitude) of the movement or deviation may provide an indication of the degree by which the user's movement has changed relative to their individualized movement profile. The direction of the deviation (e.g. direction of the arrow) may provide an indication of how the user's movement has changed relative to their individualized movement profile (e.g. staying or trending towards a non-injured state, or trending towards or already in an injured state). The processing of new movement data of the user and subgroup data may provide useful information about the runner. It is to be appreciated that the specifics relating to FIG. 4 are merely provided as an example, are placed within a two-dimensional subspace (to illustrate how the subgroup analysis may be used), and are not meant to be limiting.

Referring back to FIG. 3, the process at block 307 assesses the new movement data to interpret the amount and/or direction of deviation in the new movement data. The process may determine if the user's newly observed atypical movement pattern has led to a change in their subgroup assignment. The determination may be performed with the use of a supervised machine learning algorithm. Any suitable supervised machine learning algorithm may be used, for example support vector machine, linear discriminant analysis, neural network, random forest, etc. For these supervised algorithms, movement data may be organized as a set of wearable sensor variables over a large number of different users or data collections sessions. Therefore, contrary to the unsupervised methods where data was organized as many individual movement segments within one individual, these data would be organized as a single average set of the wearable sensor variables from each user's movement segment data, across many other users, for example average variables of one user/data collection×multiple users/data collections. In one embodiment using a support vector machine, movement sensor data is organized in the above-mentioned manner and a linear or non-linear hyperplane (e.g., plane dividing the subgroups of interest) is calculated to determine the threshold boundary between subgroups. This boundary is created by identifying support vectors (e.g., users/data collection points in the subspace) that best separate the subgroups of interest. This process involves standard methods to identify and optimize features (i.e., important variables for separating subgroups) and their weighting for classification. This classification subspace generated by these supervised machine learning algorithms may then be used to compare new movement data of a user to previously collected data from other users to determine which subgroup the current data collection session is more similar to. In other words, the process may identify a subgroup from among a plurality of subgroups that most closely corresponds to the new individual user's movement information. Further, the movement within this classification subspace, explained further below, may be used to track the progression or regression of a single user over time.

The movement information of users, which forms the plurality of subgroups, are labeled with one or more subgrouping predetermined characteristics. The supervised machine learning algorithm determines the one or more multivariate threshold boundaries that separate particular groups in the high dimensional data subspace. The threshold boundaries allow the new movement data collected from a user to be assessed relative to the subgroups.

In the process of FIG. 3, if the new movement data of the user indicates that the user has not changed subgroups, the process proceeds to block 308 where an output indication signal may be generated in a similar manner as in block 306. The output indication signal may indicate or otherwise cause to be indicated that the user's movement pattern is moderately atypical. In an embodiment, the output indication may be in the form of a yellow light output indicating that the new movement data is considered moderately atypical for the user under the particular external conditions.

If the new movement data of the user indicates that the user has changed subgroups, the process proceeds to block 309 where an output indication signal may be generated in a similar manner as in block 306. The output indication signal may indicate or otherwise cause to be indicated that the user's movement pattern is highly atypical since the user has changed subgroups. In an embodiment, the output indication may be in the form of a red light output indicating that the new movement data is considered highly atypical for the user under the particular external conditions.

Additionally, or alternatively, in the process according to FIG. 3, one or more of the new movement data, evaluation or comparison results on the new data relative to the user's individualized movement profile, results from a subgroup analysis, and the output indication may be saved in memory locally on the device that performed the evaluation, comparison, or analysis, and/or the device that generated the output signal or on another device. In another embodiment, some or all of this information may be transmitted to another device and saved in memory or storage of the other device.

Figure 5:
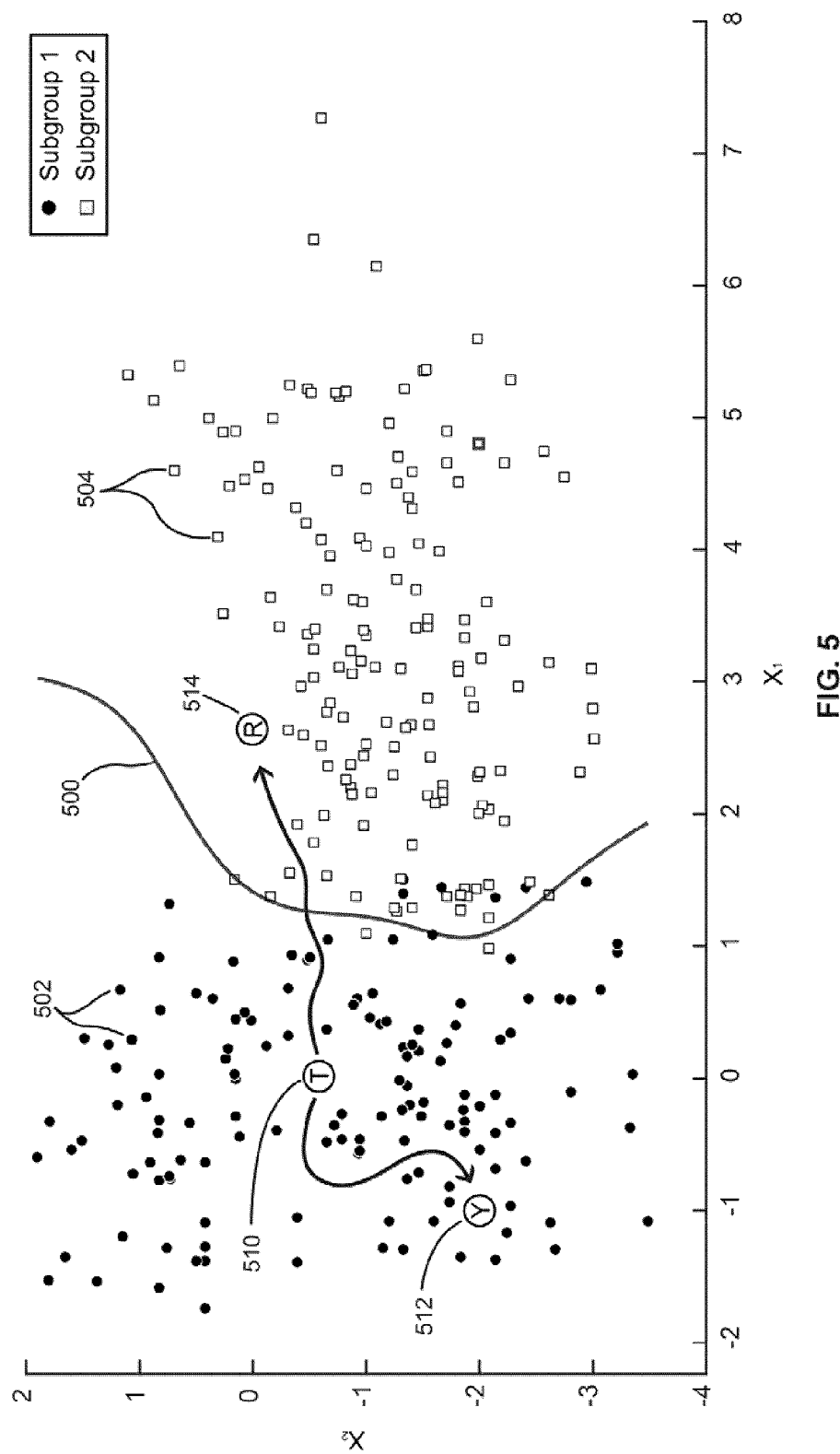
FIG. 5 is a graph of an example two-dimensional subspace consisting of two variables to illustrate how the subgroup analysis may be used.

FIG. 5 is a graph of an example two-dimensional subspace consisting of two variables ($X_1$ and $X_2$) to illustrate how the subgroup analysis may be used. Unlike FIG. 2A, where each data point represents an individual movement segment obtained entirely from one user, in FIG. 5 each data point represents a composite movement segment from a particular user. Specifically, each of the data points in FIG. 5 is an average (i.e., centroid) of all movement segments for an individual user or for a user's data collection session. The average values may be generated by a device or system according to the present disclosure based on a plurality of movement segments for each of user. Therefore, FIG. 2A illustrates the variation occurring between the many different movement segments of a single user, while FIG. 5 represents the variation occurring between different users. In this example, there are two subgroups of users, namely Subgroup 1 and Subgroup 2 as indicated with circle points 502 and square points 504. The two subgroups could be, for example, healthy female runners and injured female runners. The two subgroups are separated by boundary line 500.

Further, the typical circle T 510 represents a user's previously defined typical movement patient in their individualized movement profile that is located within their subgroup (e.g., healthy female runners). The T circle represents an average of all movement segments in the movement data for the user's typical movement pattern. FIG. 5 also illustrates two separate new data collection sessions for the user that represent two deviations from this typical pattern. First, the Y circle 512 represents an average of all movement segments in the first new movement data collected for the user. The Y circle 512 would generate a yellow light, or similar, output that indicates that the user undergoing a moderate deviation from their typical movement pattern. In other words, the user has moved out of their typical pattern (e.g. out of the subspace defined by their individualized movement profile), but the user remains in the same subgroup (i.e. has not crossed boundary line 500). This new user data is thus considered moderately atypical.

On the other hand, the R circle 514 represents an average of all movement segments in the second new movement data collected for the user. The R circle 514 could generate a red light, or similar, output that indicates that the user has undergone a significant change from their typical movement pattern. The user has not only deviated from their personal typical pattern, but the user has also moved into a completely different user subgroup (e.g., injury female runners). This new user data is thus highly atypical. In this embodiment, both the magnitude and directionality of the deviation within the subspace is used for determining the output indication to the user.

Accordingly, the Injury Risk Tracking embodiments of the present disclosure, including those described above, may provide for longitudinally and continuously monitoring of the user movements for the purpose of identifying deviations in the user's movement patterns. The present disclosure allows for the continued expansion of a user's individualized movement profile under one or several external conditions not specifically described herein. Further, the ternary output (e.g., green light, yellow light, red light) may provide an alert of movement pattern deviations, including subtle deviations that may inform short or long-term training adjustments directed by the user or a clinician. However, it should be noted that the output from this method (i.e., green light, yellow light, red light) may be presented in any other suitable way not specifically outlined here, such as, but not limited to, numerical outputs and complementary display visualizations. As an example, the output may be any form of output such as an ordinal scale of 0-10, where anything above 5 (as an example) is a moderately atypical and anything above 8 is highly atypical. Further, the Injury Risk Tracking aspects of the present disclosure provide techniques for longitudinally and continuously monitoring human movement that may be applied to any movement pattern that involves repeatable or cyclical movement segments (e.g., gait cycle, swimming stroke, cycling stroke, jump, etc.).

Performance Tracking

Features and aspects of the Injury Risk Tracking embodiments outlined above to track injury risk may be applied in embodiments for tracking the performance of a user. These embodiments may be referred to as Performance Tracking embodiments. The processes used to identify deviations from a user's individualized movement profile, as well as deviations from one or more subgroups, may be similar to those described above in relation to the Injury Risk Tracking embodiments. However, the manner in which the deviations are interpreted differs in that the user is, for example, attempting to alter their movement pattern towards a more desirable subgroup. For example, a recreational male runner may identify competitive male runners as their target subgroup. As such, the user may be looking to develop a movement pattern that is more similar to this subgroup over the course of their training. Therefore, while the techniques and processes may be similar to the previously described Injury Risk Tracking embodiments, in the Performance Tracking embodiments user movement towards the user's desired subgroup may be defined as a positive change (e.g., yellow light). Subsequently reaching the subspace containing users from the desired subgroup may be defined as reaching the user's movement pattern goal (e.g., green light). Alternatively, no movement or movement away from the desired subgroup may be considered as no change or a negative change (e.g., red light).

Rehabilitation Tracking

In addition, features and aspects of the Injury Risk Tracking and Performance Tracking embodiments outlined above may be applied in embodiments for tracking the rehabilitation of a user. These embodiments, which are referred to as Rehabilitation Tracking embodiments, may utilize similar data sources and techniques to determine a user's progress from an injured state to a non-injured state during a rehabilitation process. However, unlike the Injury Risk Tracking embodiments, the Rehabilitation Tracking embodiments utilize the subgroup analyses to compare a user's progress towards a preassigned subgroup. This subgroup may be referred to as a target subgroup. The target subgroup may be chosen by the user or by a clinician. For example, an injured competitive male runner may choose to use a rehabilitation tracking embodiment to assess their rehabilitation progress as they attempt to move from an injured movement pattern towards that of a healthy competitive male (i.e. the target subgroup).

Figure 6:
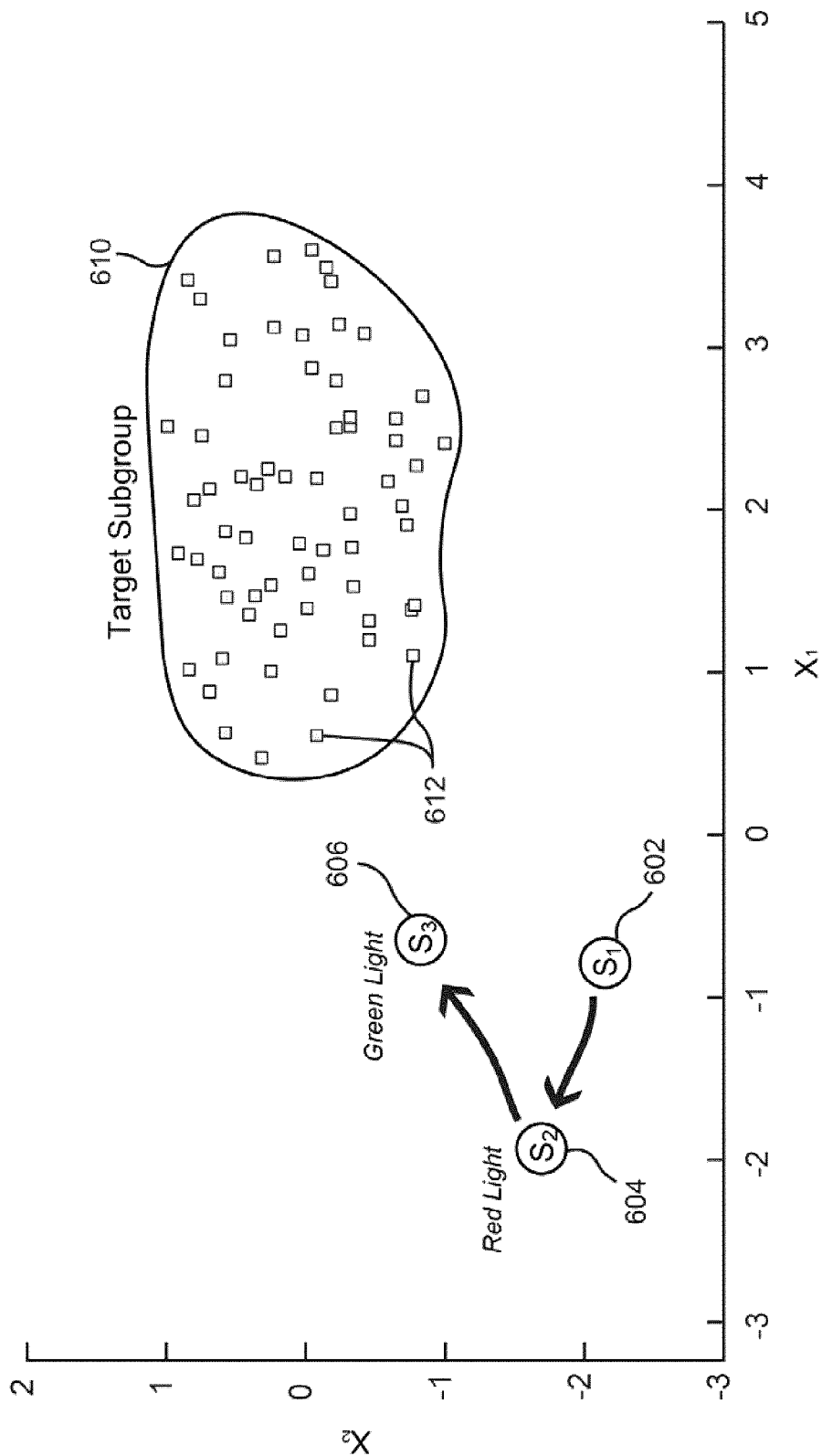
FIG. 6 is a graph of an example two-dimensional subspace consisting of two variables illustrating a rehabilitation tracking embodiment.

FIG. 6 is a graph of an example two-dimensional subspace consisting of two variables ($X_1$ and $X_2$) illustrating a rehabilitation tracking embodiment. Each data point 612 represents an individual user (e.g., average of all movement segments for a user or for a user's data collection session), similar to FIG. 5. However, in FIG. 6 all users visualized are located in target subgroup defined by boundary line 610.

In this example, three successive data collection sessions during a user's rehabilitation are presented, as indicated by $S_1$ 602, $S_2$ 604, and $S_3$ 606. Each S circle represents an average of all movement segments in the movement data for the respective data collection session. The user's target subgroup is also shown. In order to track the rehabilitation progress, a change in a user's movement pattern over successive data collection sessions is monitored in this subspace. Movement data collected from the user may be compared to previously collected movement data of the user. It may then be determined if the more recent movement data more closely or less closely corresponds to the movement data of the users of the target subgroup compared to the previously collected movement data. Specifically, movement away from the assigned subgroup (e.g., $S_1$ to $S_2$) signifies that a user's movement pattern is becoming more different from the assigned subgroup. A first output indication (e.g. a red light) may be generated for the user. On the other hand, movement towards the assigned subgroup (e.g., $S_2$ to $S_3$) signifies that the user's movement pattern is becoming more similar to the assigned subgroup. A second output indication (e.g. a green light) may be generated for the user. Furthermore, although not shown in FIG. 6, a third output indication (e.g. a yellow light) may be generated when there is no movement between successive data collection sessions of the user in the movement pattern subspace.

The Rehabilitation Tracking embodiments may be used in or outside of a clinical setting to provide a continued update on the progress of a user's rehabilitation from a movement perspective. While the use of these embodiments may not be expected to reverse permanent musculoskeletal impairments or diseases (e.g., osteoarthritis, total joint replacement, etc.), their use may be used to improve movement patterns in spite of these diseased states.

Example Electronic Device

Figure 7:
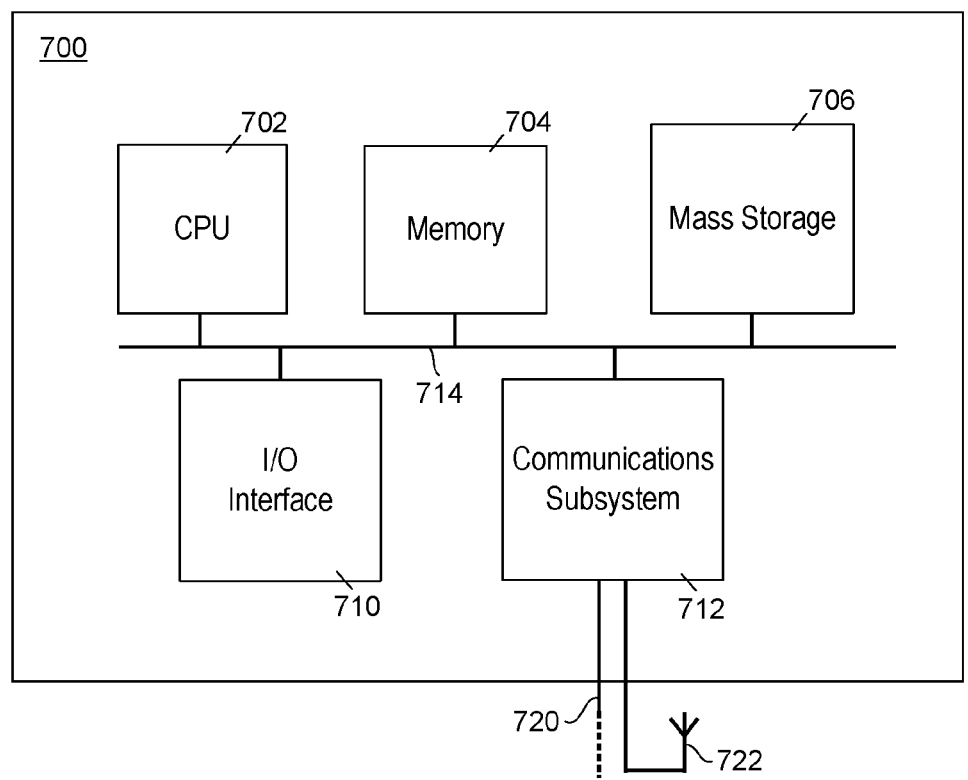
FIG. 7 is a block diagram of an example electronic device that may be used in implementing one or more aspects or components of an embodiment.

FIG. 7 is a block diagram of an example electronic device 700 that may be used in implementing one or more aspects or components of an embodiment according to the present disclosure. For example, device 700 may be or comprise a motion sensor, a physiological sensor, any other suitable type of sensor, a computing device, a smart device such as a smart watch or smart phone, a server computer, or a database computer.

The electronic device 700 may include one or more of a central processing unit (CPU) 702, memory 704, a mass storage device 706, an input/output (I/O) interface 710, and a communications subsystem 712. One or more of the components or subsystems of electronic device 700 may be interconnected by way of one or more buses 714 or in any other suitable manner.

The bus 714 may be one or more of any type of several bus architectures including a memory bus, storage bus, memory controller bus, peripheral bus, or the like. The CPU 702 may comprise any type of electronic data processor. The memory 704 may comprise any type of system memory such as dynamic random access memory (DRAM), static random access memory (SRAM), synchronous DRAM (SDRAM), read-only memory (ROM), a combination thereof, or the like. In an embodiment, the memory may include ROM for use at boot-up, and DRAM for program and data storage for use while executing programs.

The mass storage device 706 may comprise any type of storage device configured to store data, programs, and other information and to make the data, programs, and other information accessible via the bus 714. The mass storage device 706 may comprise one or more of a solid state drive, hard disk drive, a magnetic disk drive, an optical disk drive, or the like. In some embodiments, data, programs, or other information may be stored remotely, for example in the "cloud". Electronic device 700 may send or receive information to the remote storage in any suitable way, including via communications subsystem 712 over a network or other data communication medium.

The I/O interface 710 may provide interfaces to couple one or more other devices (not shown) to the electronic device 700. The other devices may include but are not limited to one or more of a sensor, a smart device, a computing device, a server, a wireless access point, a base tower, a touch sensor device, an electronic display, an indicator light (e.g. light emitting diode), a speaker, and a microphone. One or more of the output devices, for example a display, indicator light, or speaker, may be used to output an output indication signal indicating information on the deviation of a user's movement data. Furthermore, additional or fewer interfaces may be utilized. For example, one or more serial interfaces such as Universal Serial Bus (USB) (not shown) may be provided.

A communications subsystem 712 may be provided for one or both of transmitting and receiving signals. Communications subsystems may include any component or collection of components for enabling communications over one or more wired and wireless interfaces. These interfaces may include but are not limited to USB, Ethernet, high-definition multimedia interface (HDMI), Firewire (e.g. IEEE 1394), Thunderbolt™, WiFi™ (e.g. IEEE 802.11), WiMAX (e.g. IEEE 802.16), Bluetooth™, Wireless Body Area Network (e.g. IEEE 802.15.6), or Near-field communications (NFC), as well as GPRS, UMTS, LTE, LTE-A, dedicated short range communication (DSRC), and IEEE 802.11. Communication subsystem 712 may include one or more ports or other components 720 for one or more wired connections. Additionally or alternatively, communication subsystem 712 may include one or more transmitters (not shown), receivers (not shown), and/or antenna elements 722.

The electronic device 700 of FIG. 7 is merely an example and is not meant to be limiting. Various embodiments may utilize some or all of the components shown or described. Some embodiments may use other components not shown or described but known to persons skilled in the art.

To gain a better understanding of the teachings and disclosures described herein, the following examples are set forth. The examples are not intended to limit the scope of the present disclosure in any way. In some instances, the examples may provide additional features and/or embodiments of the present disclosure.

Example 1

In this case study, an experience female runner, who runs more than 30 km per week, is tracked over a number of runs using the methods and/or devices according to the present disclosure. The data presented here are from a research study involving 41 participants (30 female, 11 male) that completed a total of 724 runs. Specifically, the female runner featured in this case study, meaning the user whose movement data was analyzed, completed a total of 7 runs, but developed pain in her final 2 runs and thus is an excellent demonstration of the process and utility of the teachings according to the present disclosure.

Data Analysis

Six movement information variables were collected from every runner using multiple wearable sensors for each of the 724 runs. One sensor was an accelerometer and was secured to the lower back in order to collect the following data: pelvic drop (measured in degrees of motion), pelvic rotation (measured in degrees of motion), ground contact time (measured in milliseconds), vertical oscillation (measured in centimeters), braking (measured in meters/second), and cadence (measured in steps/minute). Other sensors were part of a smart watch, which was worn on the user's preferred wrist in order to collect the following data: heart rate (measured in beats per minute), altitude (measured in meters), distance (measured in kilometers), global position latitude (measured in degrees), global position longitude (measured in degrees), and running speed (measured in meters/second).

These data were used in three primary analyses: (1) a within subject analysis to determine the external conditions (e.g. terrain, route, speed, etc.) for each individual data collection session using data from the smart watch, (2) a within subject analysis in order to identify the featured runner's typical gait pattern using the data collected from the lower back sensor and (3) a subgroup analysis to present movement pattern deviations in the context of subgroups of users, based on data collected from the lower back sensor.

For the featured runner, the data from the lower back accelerometer sensor from the first two runs were used to determine her typical movement pattern boundary using the techniques according to an unsupervised machine learning method. Specifically, throughout these initial two runs, the six movement information variables from the lower back accelerometer sensor were measured over a total of 1,400 movement segments. Therefore, the data collected over these initial runs was organized as a 6×1,400 matrix of data that was used to define the runner's typical movement pattern using an unsupervised principal component analysis and a one-class support vector machine. The six variables were transformed into six new and linearly uncorrelated variables, known as principal components via a principal component analysis, to reduce potential redundancy in the variables. The subsequent data set resulted in 6 principal component scores and these transformed variables were then used to determine the multivariate boundary and to define the typical data using a one-class support vector machine method.

Using data from both the accelerometer lower back sensor, and the smart watch wrist sensors, all following runs were compared to this typical movement pattern in order to determine (1) if the external conditions were the same, or different compared to the typical runs, using the smart watch sensor data and (2) if the majority of the movement segments were within, or outside of these boundaries, using the data from the accelerometer lower back sensor. This typical movement pattern boundary can be presented in a within subject analysis, as in FIG. 2A, where each movement segment is plotted as an individual data point 202. However, these data may also be presented in comparison to other users, as in FIG. 5, which allows for the visualizations of deviations from each run as a whole, when placed in comparison to other subgroups. For ease of interpretation, only the latter is presented in the current case study (i.e., subgroup plot) as it allows for the visualization of atypical data as either moderately atypical (e.g., yellow light) or highly atypical (e.g., red light).

Results and Discussion

In this experiment, using the data from the smart watch wrist sensors, it was determined that the runs completed by each of the participants fell within the same set of external conditions (e.g., terrain, route, speed, etc.) and therefore, only one typical movement pattern boundary was required for each individual.

Figure 8:
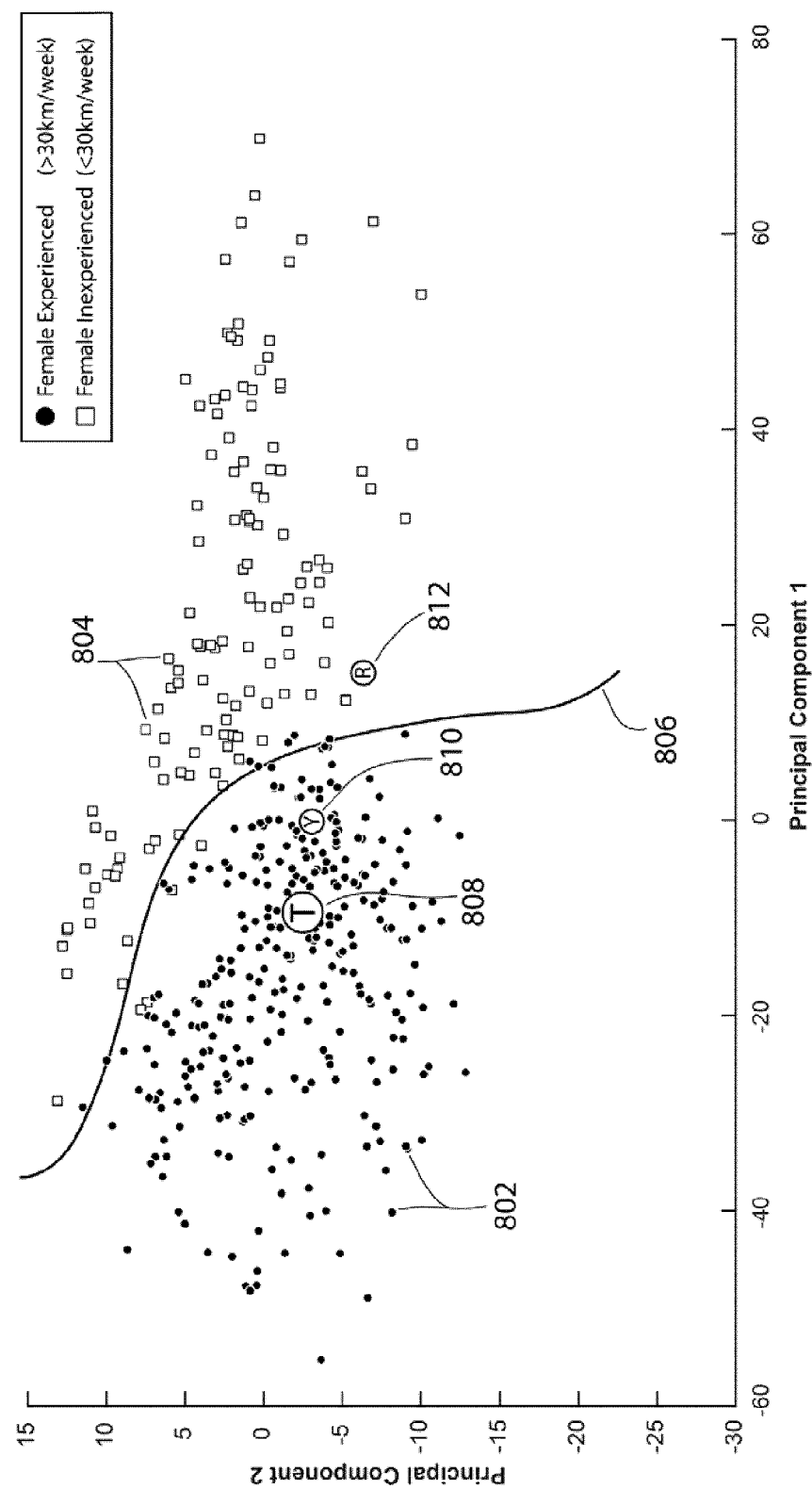
FIG. 8 is a graph of a two-dimensional subspace that compares a subgroup of experienced female runners to a subgroup of inexperienced female runners.

FIG. 8 is a graph of a two-dimensional subspace that compares a subgroup of experienced female runners represented by the solid circular data points 802 to a subgroup of inexperienced female runners represented by the square data points 804. A decision boundary line 806, obtained from a non-linear support vector machine mathematical approach, separates the data points of these subgroups of runners. Further, to illustrate the position of the featured female runner in this subspace, the centroid of her typical movement pattern, calculated from the first two runs, is represented by T circle 808. It can be seen that this centroid 808 is clearly within the subspace of female experienced runners, as would be expected. Using the data from the lower back sensor, it was determined that the two subsequent runs for the featured female runner that followed the initial runs were located within her typical movement pattern boundary, and were therefore deemed typical (e.g., green light). These runs are not shown in the graph of FIG. 8.

However, the featured runner deviated from her typical pattern with the next run session as represented by Y circle 810. In other words, the majority of the movement segment data from this new run session were outside of the previously defined typical boundary. Specifically, an overall Euclidean distance of 9.6 units was observed between session Y 810 and the featured runner's typical pattern T 808 in the FIG. 8 subspace. Importantly, the runner did not report any pain or anything unusual during this run. However, according to an embodiment of the present disclosure, this run is deemed as moderately atypical as it is located outside of the runner's typical movement pattern, but remained in the subspace of the subgroup that she would be expected to be located within, that of other female experienced runners. Therefore, an output indication signal is generated indicating that the movement pattern for this particular run was moderately atypical (e.g., yellow light).

The next two runs by the featured runner were accompanied by pain during movement and movement data from one of these runs is represented by R circle 812. The data collected during this session is located outside of the runner's typical gait pattern. The collected data is also outside of the user's expected subgroup (experienced female runners) and is instead located within the subgroup of inexperienced female runners. Specifically, an overall Euclidean distance of 25.1 units was observed between this session R 812 and the featured runner's typical pattern T 808 in the FIG. 8 subspace. This information tells us that this runner was no longer exhibiting a running movement pattern similar to her typical pattern or similar to a subgroup of experienced female runners. Rather, the runner's movements during run session R 812 were more similar to a subgroup of inexperienced female runners. Therefore, this run is deemed highly atypical and an output indication signal may be generated indicating that the movement pattern for this particular run was highly atypical (e.g., red light).

Conclusion

The results presented here show that an embodiment according to the present disclosure defined an individual runner's typical gait pattern T 808, but at some point during the runner's training, the runner's movement pattern began to change as indicated by Y 810. This change preceded the physiological response of pain and as such, a device or system according to the present disclosure would present an output indication representing a warning to this runner (e.g. yellow light). However, without this output indication being presented to the runner, the runner may have continued her training and reached a point where she experienced pain and exhibited further movement pattern changes. Given that the runner was still able to run through this level of pain, it is possible that if she carried on without any change or alteration in movement patterns, she would continue towards greater pain and a potentially more serious injury. Therefore, this case study demonstrates the ability of the present disclosure to define an individual's typical running pattern, identify an individual runners' atypical movement pattern, and identify subtle changes in movement patterns that precede this physiological response of pain and would be important for training alterations.

Example 2

In this further case study, movement data was collected from an inertial measurement unit (IMU) placed on the lower back for 28 subjects running a marathon race (42.2 km) to better understand the effects of fatigue over the course of a prolonged run. One male recreational runner with eight years of running experience (>30 km/week) sustained a running-related injury in his left calf muscle just after the half-way point of the 2017 Calgary Marathon race and retired near the 28 km-mark. In this case study, machine learning methods (i.e., one-class support vector machine) were used to identify the 'typical' pattern for the injured runner at the beginning of the race and detect how his patterns became 'atypical' prior to retiring from the race. The injured runner's patterns were compared to data from the 27 healthy runners who finished a marathon to demonstrate the greater atypical changes that may have been indicative of injury.

Data Collection and Analysis

Participants were instructed to run at their own desired race pace, and six biomechanical variables were continuously recorded throughout the marathon race. The observations from the IMU were aligned with the output of a wrist-worn GPS watch so that the biomechanical data was known at each race distance. If at any point the runner's speed was slower than 1.8 m/s, which is approximately the minimum speed of the run-walk transition, then these data points were removed from analysis. Running biomechanics are also affected by graded running, so the elevation grade was calculated using altitude and distance data from the GPS-watch and retained data pertaining to level running (i.e., −2%<x<2% grade) for analysis. Each dataset was then reduced by removing 0-4 km of the marathon race data to ensure that runners were properly warmed-up and to remove any potential irregular running data associated with running alongside the large cluster of runners at the beginning of organized race events. The next 10 km (4-14 km) were considered the 'typical' run, and the remaining data (up until injury) were partitioned into 2-km test sections throughout the marathon (i.e., 14-16 km, 16-18 km, 20-22 km, 22-24 km, 24-26 km, 26 km-Injury), resulting in 8 sections (1 typical and 7 test) for analysis.

A one-class support vector machine (SVM) was trained and cross-validated on data from the six biomechanical variables from the typical run for each runner independently, assuming 5% of the observations were outliers (Nu=0.05). The SVM classification model was then applied to each runner's test datasets, in an unsupervised fashion, to determine the percentage of observations that were deemed anomalous (or atypical).

Results and Discussion

Figure 9:
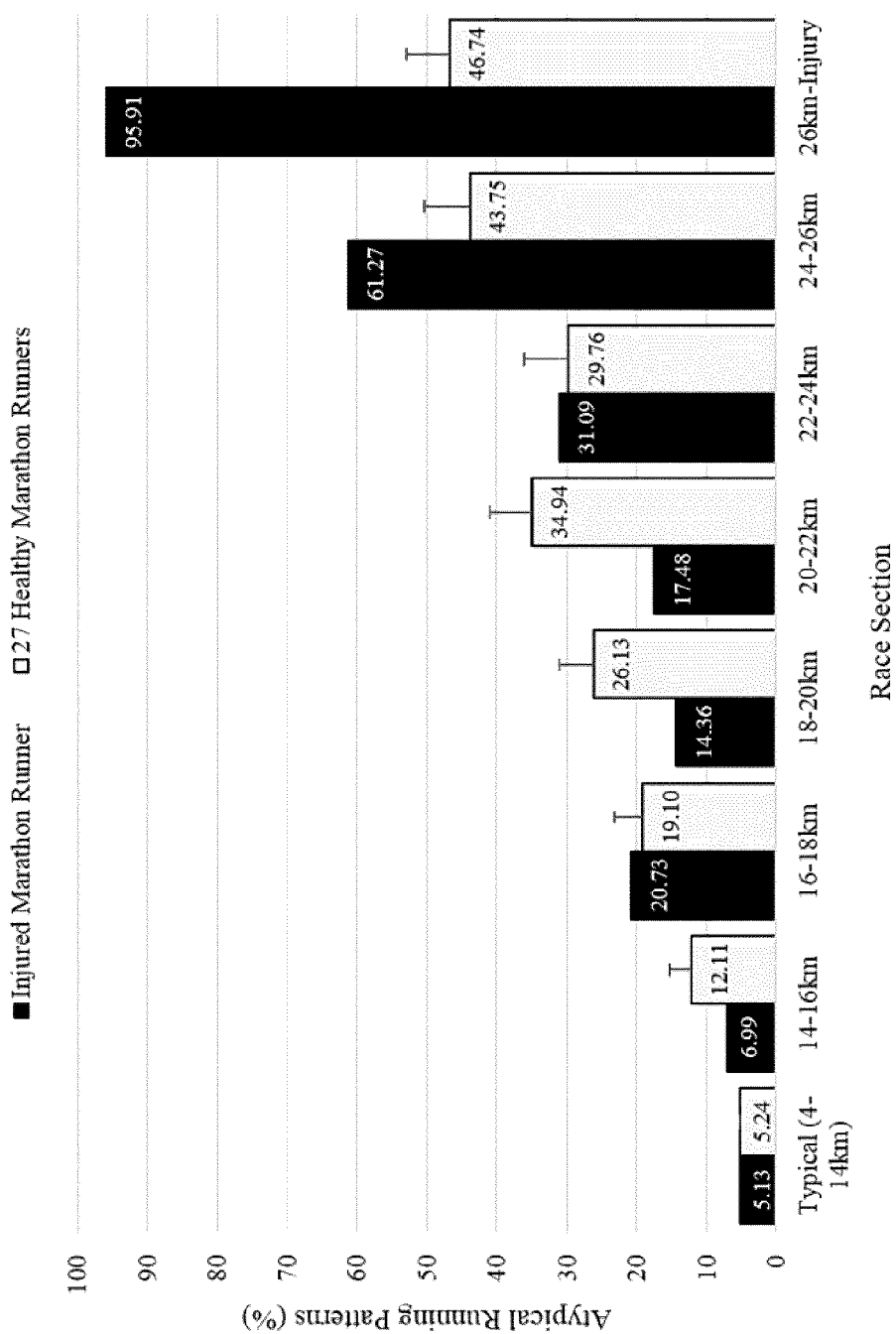
FIG. 9 is a graph showing the percentage of atypical running patterns for an injured runner and health marathon runners over various intervals of a race.

FIG. 9 is a graph showing percentage of atypical running patterns for the Injured Runner and Healthy Marathon Runners. The error bars represent the standard error of measurement (SEM).

The results indicate that for the first half of the marathon race, the percentages of atypical observations for the injured runner were comparable to the healthy runners. Then, at 22-km, the percentage of atypical observations increased for the injured runner, and it further increased exponentially thereafter until he was no longer able to finish the marathon race (see FIG. 9). The runner provided a reflective statement on his injury during the marathon, and the sharp increase in atypical observations at the 22-24 km marathon section corresponded with the onset of pain associated with knots in his left calf. Furthermore, the subject-specific model was able to detect an exponential increase in atypical running patterns for the remainder of his run, even though he said he "felt comfortable" between 24-26 km. Prior to retiring from the race due to injury (at approximately the 28-km mark), 95.91% of his running data were classified as atypical.

Conclusion

Fatigue-related running biomechanics can be highly individual, and each runner has a certain level of uniqueness to their gait pattern. Thus, single-subject methods may be useful to assess individual changes under different conditions. In this case study, a novel method using machine learning with wearable sensor data was demonstrated to detect fatigue- and injury-related changes in running patterns. The injured runner's patterns were also compared to an uninjured control group to demonstrate the atypical changes that may have been indicative of injury. Specifically, the sharp increase in atypical running data for the injured subject during the 20-22 km section corresponded with his reported onset of calf pain, and atypical running data increased exponentially throughout the run, even though he "felt comfortable" between 24-26 km. Prior to retiring, 95.91% of his running data was not only atypical, but it was also considerably greater than the uninjured group's atypical running patterns from fatigue alone.

In conclusion, these methods were able to detect atypical running patterns associated with pain in real-time. Based on this achievement, it is expected that the collection of longitudinal subject-specific biomechanical data of healthy recreational runners may be effective to identify changes in biomechanics that may precede injury.

Example 3

In this further case study, a machine learning approach was developed and used, using wearable sensor data, to identify subject-specific changes in gait patterns related to improvements in clinical outcomes. Specifically, the objective of this case study was to establish a proof-of-concept of a subject-specific one-class model's ability to identify clinically relevant changes in gait patterns over the course of rehabilitation. Specifically, a goal was to determine whether changes in gait patterns correlated with clinical improvements following a 6-week exercise intervention in knee OA patients. It was hypothesized that patients who benefited most from the exercise intervention (i.e., improvements in self-reported pain, function, etc.) would also demonstrate the greatest changes in their gait patterns (i.e., increased percentage of outlier gait cycles) following the intervention, as assessed by a Spearman's rank correlation ($\alpha<0.05$).

Methods

Subjects

A subset of 8 knee OA patients (Sex: 4F/4M, Age: 58 (5) years, Body Mass Index: 25.3 (4.8) kg/m$^2$, walking speed: 1.1 (0.15) m/s) were analyzed from a larger exercise intervention. These patients were selected for the current analysis as they completed two baseline gait trials before the intervention, as well as one gait trial post-intervention. All participants were required to be radiographically diagnosed with knee OA and able to walk without assistive devices.

Protocol

Figure 10:
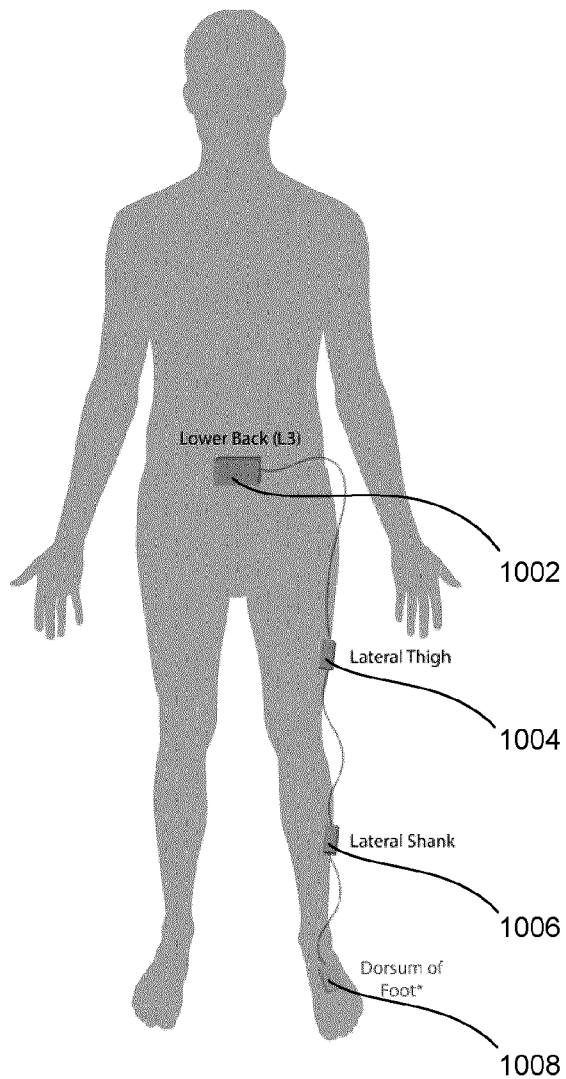
FIG. 10 is a diagram showing example placements of inertial sensors on an affected side of a leg of knee osteoarthritis patients.

Participants completed two baseline gait trials on different days, within one week of beginning the exercise intervention. In each session, participants wore four wearable inertial sensors (iNEMO inertial module, STmicroelectronics, Geneva, Switzerland) securely fastened to their lower back (approximately the L3 vertebrae), lateral thigh, lateral shank, and dorsum of the foot on the most affected leg. FIG. 10 is a diagram showing example placements of inertial sensors 1002, 1004, 1006, 1008 on the most affected side of a leg of knee osteoarthritis patients. The dorsum of foot sensor 1008 was only used for event detection and gait cycle segmentation. In order to safeguard against potentially high impact accelerations at the foot, the highest accelerometer and gyroscope range setting (acceleration range ±16 g, gyroscope range ±2,000°/s, sampling rate 100 Hz) was used for dorsum of foot sensor 1008. Further, the same range settings were selected across all remaining sensors to maintain data consistency. While all four sensors 1002, 1004, 1006, 1008 collected both linear acceleration and angular velocity data, only linear acceleration data from the three most proximal sensors (i.e., lower back 1002, thigh 1004, and shank 1006) were used for modeling the subject-specific gait patterns. The dorsum of foot sensor 1008 was used solely for gait event detection, to be discussed in the following section.

All participants walked on a level treadmill (Bertec, Columbus OH, USA) fora short acclimatize period at a self-selected pace, before 2.5 minutes of data were collected. A trial length of 2.5 minutes was used to obtain a minimum of 100 gait cycles per session, as this has been a recommended for similar machine learning analyses. The same protocol and self-selected pace were used during the post-intervention gait trial. Participants also completed a Knee injury and Osteoarthritis Outcome Score (KOOS) before and after the intervention to assess potential changes in self-reported pain, symptoms, function in daily living, and knee related quality of life following the intervention. The exercise intervention itself was a 6-week therapist-directed, hip-focused muscle strengthening intervention detailed in Kobsar et al., 2017.

Data Analysis

Pre-Processing

Linear acceleration data underwent a static attitude correction to align each sensor with the global vertical and horizontal planes. Following this correction, all 3D linear acceleration and angular velocity data were filtered with a 10 Hz low-pass 4th order recursive Butterworth filter. The angular velocity data of the dorsum of foot sensor 1008 was used to determine gait events (e.g., initial contact and toe-off) in a manner previously validated. Specifically, initial contact and toe-off events were determined as the zero-crossing preceding stance and the negative peak following stance in the angular velocity signals about mediolateral axis, respectively. These gait events allowed for gait cycle segmentation and time-normalization of all sensor data (e.g., 60 points for stance; 40 points for swing). Three-dimensional linear accelerations were concatenated within each sensor (i.e., 3 axes×100 data points combined to a 1×300 vector) and across all 3 sensors (i.e., 1×300 vectors from back 1002, thigh 1004, and shank 1006 sensors combined) to form a 1×900 vector which defined the overall movement pattern for each individual gait cycle. Finally, the linear acceleration data from each gait trial were stored in an m×900 matrix, where "m" equals the number of gait cycles recorded during the 2.5 minutes of data collection. The average number of gait cycles per session was 135 (10).

Data Reduction and Feature Selection

Prior to computing the boundaries of the subject-specific one-class model, the 900 point vectors defining each gait cycle were reduced to a set of principal components (PCs). To do so, data from both baseline gait trials were combined, resulting in an average of 270 gait cycles collected over 5 minutes of walking data. These data were then standardized to a mean of 0 and a standard deviation of 1, before being transformed into linearly uncorrelated PCs using a principal component analysis. The PCs that explained at least 95% of the total variance in the original data were selected as features for the algorithm. Therefore, the scores on these PCs across all baseline gait cycles were used as the features to define the overall gait pattern of a subject. Given that this was a subject-specific model, a total of 8 principal component analyses were conducted on baseline data (i.e., one for each subject). Therefore, each patient had their own unique set of gait features to be used in modeling their gait pattern. Post-intervention data were reduced and features (i.e., PC scores) were computed in the same manner as the baseline. This procedure involved utilizing the data reduction outputs generated from the baseline data (i.e., mean, standard deviation, and PC loading coefficients) to ensure the post-intervention PC scores were appropriately aligned with their corresponding baseline data.

Defining Subject-Specific One-Class Models

Subject-specific, one-class models were defined using baseline gait features (i.e., reduced PC scores) in conjunction with a one-class support vector machine (OCSVM). The OCSVM requires only one example, or class of data (i.e., positive cases), which are used to maximize the space between these data and the origin in high-dimensional feature space. In essence, this approach attempts to define and minimize a hypersphere wherein most of the data are found and thereby define a "typical" observation or gait cycle data set. This decision boundary can then be used as a classifier to determine if new data fits within this hypersphere (i.e., positive case or "typical" gait cycle) or outside of this hypersphere (i.e., negative case, "atypical", or outlier gait cycle). This method has been shown to be successful in detecting outlier cases across a number of different machine learning applications. The boundary definition for this classifier was trained using the baseline features retained following the above-mentioned data reduction technique (i.e., PC scores depicting 95% of total variance). The training of this boundary was done using a Gaussian kernel function, in combination with a "v" parameter for regularization. This parameter was chosen based on the value that achieved less than 1% outliers in a randomly selected 20% cross-validation set from baseline data. In other words, the OCSVM decision boundary was set wide enough to include 99% of the baseline gait cycles and thereby define a "typical" gait cycle data set. It should also be noted that to ensure the method was entirely subject-specific, this regularization parameter definition was conducted separately within each individual. Finally, post-intervention data were tested to determine the percentage of gait cycles that were defined as outliers given the baseline-derived multivariate boundary threshold.

Figure 11A:
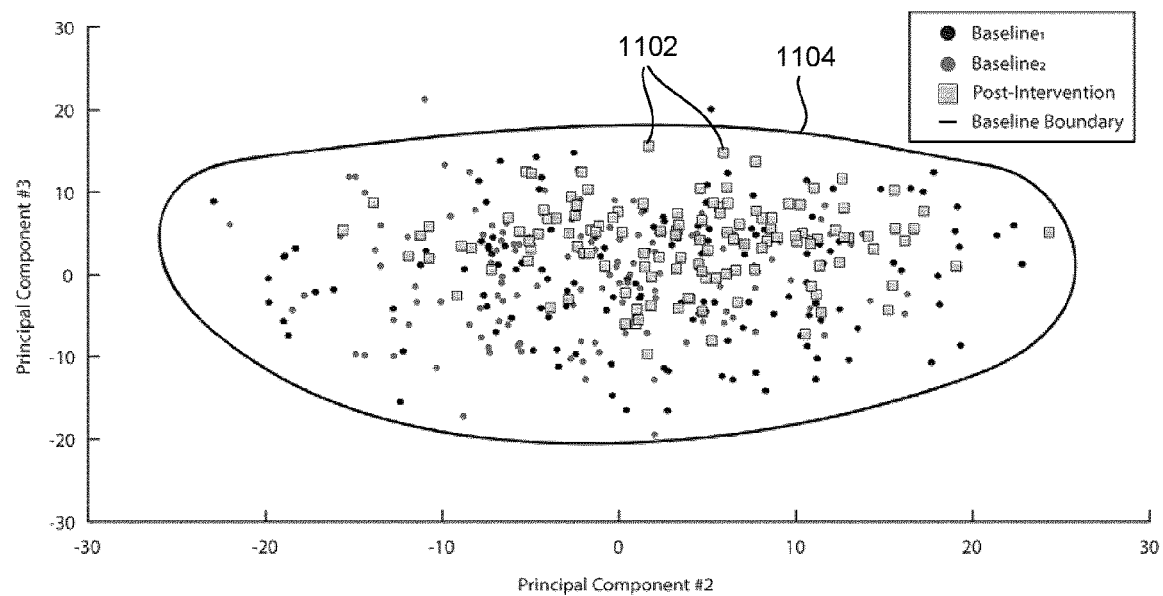
FIG. 11A is a graph of an example two-dimensional subspace consisting of two variables collected with a wearable motion sensor on a user where no post-intervention gait cycles fell outside the baseline-defined boundary.
Figure 11B:
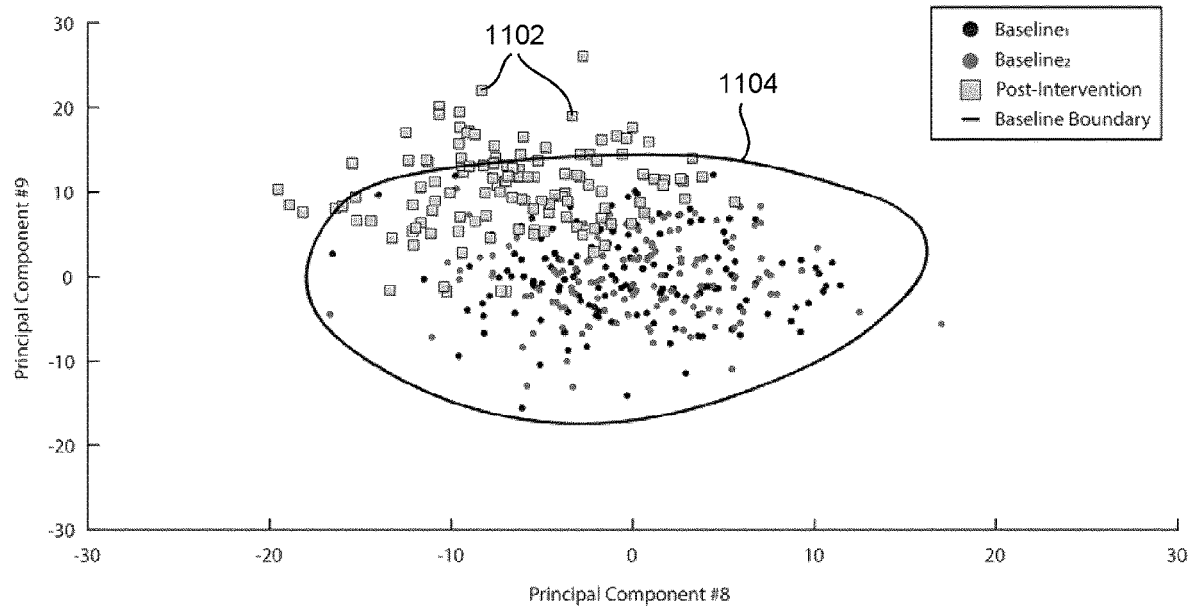
FIG. 11B is a graph of an example two-dimensional subspace similar to the one of FIG. 11A but where a large a number of post-intervention gait cycles fell outside the baseline-defined boundary.

Two simplified visualizations of this boundary definition, using only 2 PCs, are shown in FIGS. 11A and 11B. FIG. 11A shows an example where no post-intervention gait cycles 1102 fell outside the baseline-defined OCSVM boundary 1104 (i.e., 0% outliers), suggesting no change in gait patterns following the intervention. Alternatively, in FIG. 11B, a large number of post-intervention gait cycles 1102 fell outside the baseline-defined OCSVM boundary 1104 (i.e., approximately 30% outliers), suggesting the patient's gait pattern has changed in response to the intervention. However, it should again be noted that the OCSVM boundary and subsequent results were based on a high-dimensional PC space for each subject. Alternatively, these examples in FIGS. 11A and 11B represent only a 2-dimensional sub-space for ease of visualization and understanding.

Statistical Analysis

The primary variables of interest were: i) percentage of gait cycles defined as outliers in the post-intervention gait trial; and ii) average improvement in self-reported subscales of pain, symptoms, function in daily living, and knee related quality of life (i.e., post-intervention scores—baseline scores). A non-parametric correlation, Spearman's rank correlation (p), was used to assess the association between these two variables. A correlation of 0.10-0.29, 0.30-0.49, and 0.5+ were interpreted as small, medium, and large, respectively. Any subjects that reported no change or negative change were assessed as a zero-net change, based on the purpose of identifying the relationship of gait pattern deviation to clinical improvements.

Results

Figure 12:
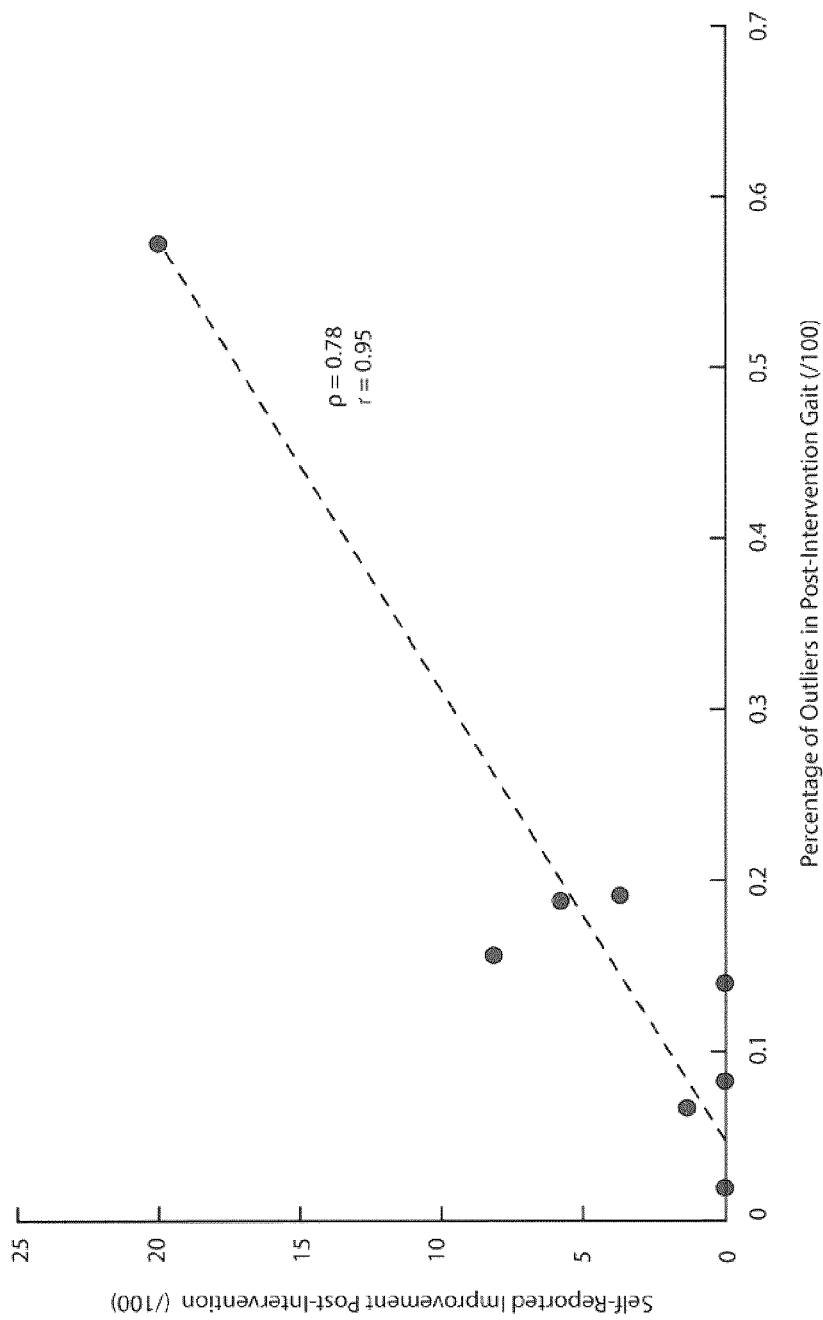
FIG. 12 is a graph showing the percentage of outlier in post-intervention data displayed a large association with the self-reported improvement in post-intervention according to an example.

The average number of PCs retained to describe 95% of the total variance in each subject was 84 (5). The average percentage of gait cycles defined as outliers in the 20% cross-validated baseline data and post-intervention gait trial data were 0.5 (0.4)% and 17.7 (17.1)%, respectively. The best regularization parameters (v) selected for the single-subject boundary thresholds were found to range between 0.1-0.8, with an average value of 0.4 (0.3). The percentage of outlier gait cycles in the post-intervention gait session achieved a large association (p=0.78; p=0.02) with the improvement in self-reported clinical outcomes following the intervention. This association, with non-parametric (Spearman rank correlation; p) and parametric coefficients (Pearson's correlation; r), is visualized using a scatter plot in FIG. 12, showing the percentage of outlier in post-intervention data displayed a large association with the self-reported improvement in post-intervention (i.e., change in Knee Injury Osteoarthritis Outcome Scores subscales): Spearman rank correlation (p)=0.78 and Pearson correlation coefficient (r)=0.95.

Discussion

A purpose of this study was to establish a proof-of-concept for the use of a machine learning approach for assessing patient-specific changes in gait following an exercise therapy intervention. In support of the hypothesis, patients who benefited most from the exercise intervention also demonstrated the greatest overall change in gait patterns, as defined by the single-subject OCSVM models. This finding was demonstrated by the significant association (p=0.78; p=0.02) between the percentage of outlier gait cycles observed in post-intervention gait and clinical outcome improvement. In the context of previous univariate models examining the association of changes in muscle strength ($r^2$=0.28-0.31) or pain sensitization (p=0.28-0.35) to changes in self-reported outcomes in knee OA patients following exercise, the current association is comparatively large. It is believed that this is the first study to integrate pattern recognition algorithms with wearable technology to define objective, subject-specific biomechanical outcomes related to clinical improvements. Moreover, the current findings support the recent recommendation of utilizing subject-specific models in wearable sensor research.

In general, these findings demonstrate a number of important concepts to be discussed. The current case study introduced a 6-week exercise intervention to uniquely identify presumably positive deviations from a knee OA patient's "typical" pattern, rather than examining artificially perturbing their gait or examining changes related to injury/fatigue. Further, it involved multiple sensor (3) and baseline patterns (2) in an OCSVM to define typical patterns. Moreover, perhaps a most important concept in the current case study was the manner in which the features and threshold parameters were selected. Specifically, a completely unsupervised approach was used, with no a priori feature selection or information of how a patient's gait may or may not change. In doing so, it was possible to define a holistic and objective measure of subject-specific changes in gait mechanics following an exercise intervention, something rarely seen in previous OA research.

While exercise interventions have consistently demonstrated improvements in the pain and function of knee OA patients, identifying concomitant changes in gait patterns has been rarely reported using conventional group-based methods. Given that much of this research has examined single, discrete variables (e.g., knee adduction moment), the sensitivity of this type of univariate statistical approaches is questionable. In contrast, the current study supports previous research suggesting examining multivariate and/or multi-segment changes may better quantify the overall biomechanical changes that occur after an exercise intervention. Nevertheless, these multivariate changes often remain limited when assessed in conventional group-based analyses. This further suggests that exercise interventions may not elicit any consistent change in gait patterns, univariate or multivariate, across heterogeneous diseases such as knee OA. Therefore, a significant strength of the current study is the introduction of an alternative, single-subject model to track multivariate, multi-segment changes in gait biomechanics. Further, this approach is directly aligned with the ongoing shift towards precision medicine and personalized treatment approaches.

Figure 13A:
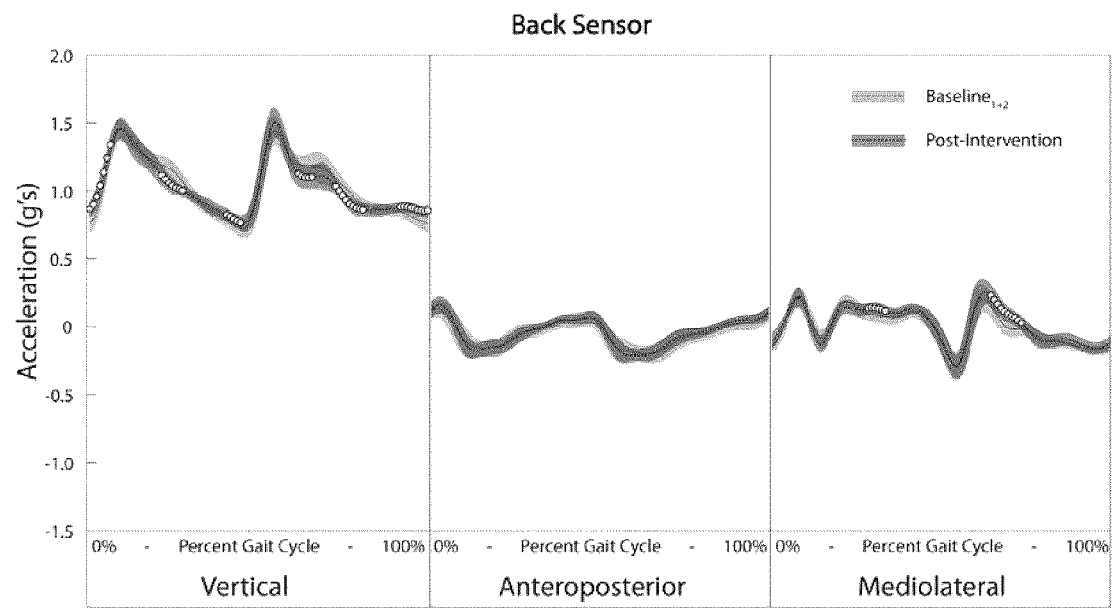
FIGS. 13A-13C are graphs showing results from motion sensors positioned at a back, a thigh, and a shank location, respectively.
Figure 13B:
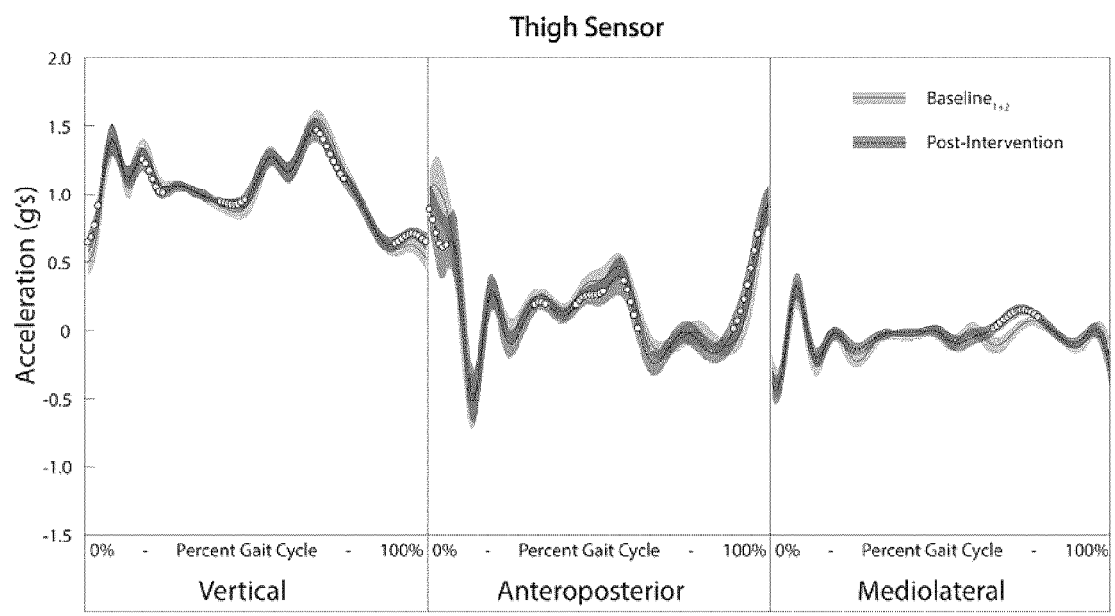
Figure 13C:
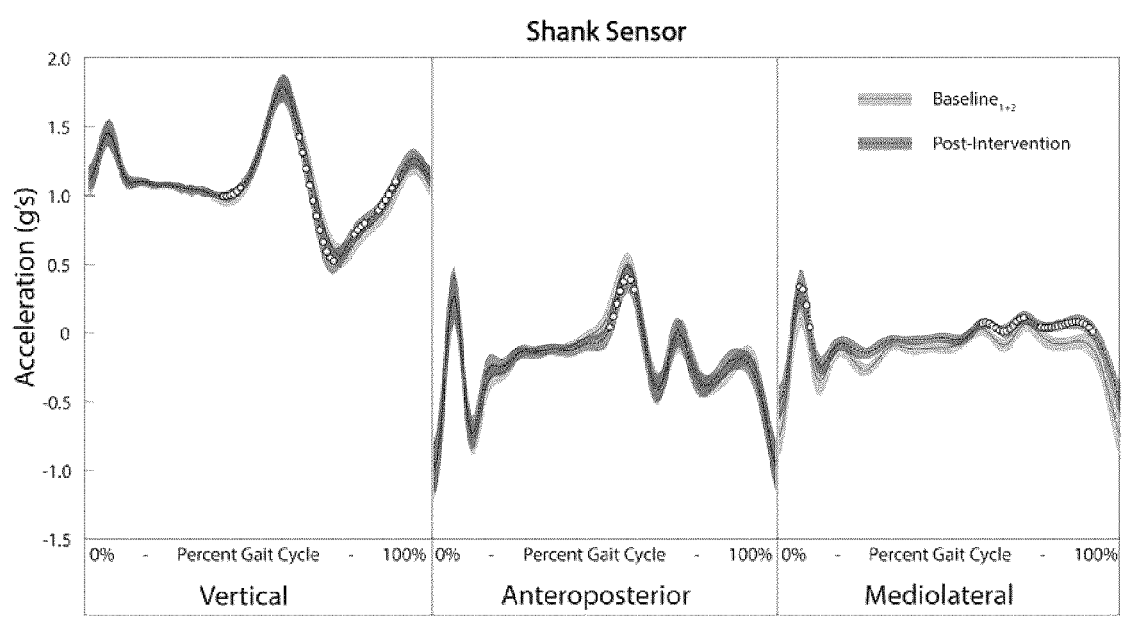

Given the complex nature of the proposed analysis, it becomes increasingly important to concentrate on ways to translate this information to the clinician and patient in a relevant and meaningful manner. The first and most simplistic way to translate this information is in the form of a percentage score from 0% to 100%, with 0% being no change in gait pattern and 100% being a complete change in overall gait pattern. In this instance, the output becomes easily interpretable, but a somewhat black box assessment of the overall change. Alternatively, these holistic changes in gait patterns could be further stratified into sensors/segments and planes of movement to identify which sensors and axes were most important in driving the overall change. Finally, a more conventional waveform analysis could be used to examine the specific changes that may have occurred in relation to the baseline boundary. A brief representative example of this analysis is presented in the graphs of FIGS. 13A-C. FIG. 13A shows results obtained from a back sensor. FIG. 13B shows results obtained from a thigh sensor. FIG. 13C shows results obtained from a shank sensor. In this example, while the thigh sensor (e.g. FIG. 13B) appears to contain the most important changes for this individual, it is evident that there are a number of multi-segment changes occurring as well. Although many of these changes appear subtle, it remains unclear whether such changes accumulating over thousands of gait cycles per day may relate to a clinically important change in the mechanical loading of the knee joint.

Conclusion

The current case study is a successful demonstration of the use of a subject-specific one-class model for identifying individualized changes in gait patterns in response to an exercise intervention. The changes in gait patterns observed with this method were found to be associated with improvements in self-reported clinical measures, following the 6-week rehabilitation protocol. Therefore, this novel method effectively integrates machine learning and wearable technology to provide an objective and evidence-informed way to understand clinically important changes in human movement patterns.

CLOSING REMARKS

The present disclosure therefore generally provides improvements in wearable sensor technology, and more specifically to improvements in wearable sensor technology devices, systems, and methods. The improvements to this technology include improvements to the functioning of electronic devices and systems to provide more useful and effective sensing and tracking capabilities.

In the present disclosure, the terms "motion" and "movement" are generally used interchangeably and are intended to have the same meaning unless explicitly indicated otherwise.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The structure, features, accessories, and alternatives of specific embodiments described herein and shown in the Figures are intended to apply generally to all of the teachings of the present disclosure, including to all of the embodiments described and illustrated herein, insofar as they are compatible. In other words, the structure, features, accessories, and alternatives of a specific embodiment are not intended to be limited to only that specific embodiment unless so indicated.

In addition, the steps and the ordering of the steps of methods described herein are not meant to be limiting. Methods comprising different steps, different number of steps, and/or different ordering of steps are also contemplated.

For simplicity and clarity of illustration, reference numerals may have been repeated among the figures to indicate corresponding or analogous elements. Numerous details have been set forth to provide an understanding of the embodiments described herein. The embodiments may be practiced without these details. In other instances, well-known methods, procedures, and components have not been described in detail to avoid obscuring the embodiments described.

The above-described embodiments are intended to be examples only. Alterations, modifications and variations can be effected to the particular embodiments by those of skill in the art without departing from the scope, which is defined solely by the claims appended hereto.

What is claimed is:

1. A device comprising:
   at least one computer processor;
   computer memory in communication with the at least one computer processor and for storing computer executable instructions, which when executed by the at least one computer processor cause the at least one computer processor to perform operations comprising:
      receive individualized movement profile information for a user, wherein the individualized movement profile information defines a subspace in which movements of the user are considered typical for the user, and wherein the individualized movement profile information corresponds to external condition information for providing context to the individualized movement profile of the user;

receive new movement information of the user relating to a physical activity from one or more wearable motion sensors;

receive new external condition information associated with the new movement information;

determine if the movements of the user during the physical activity are typical for the user by determining if the movements according to the new movement information are located within the subspace;

generate, in response to determining that the movements of the user during the physical activity are typical for the user, a first output indication signal;

identify, in response to determining that the movements of the user during the physical activity are not typical for the user, a subgroup from among a plurality of subgroups that most closely corresponds to the new movement information, wherein each subgroup consist of movement information of users all sharing on one or more predetermined characteristics, wherein each subgroup defines a subspace associated with the one or more predetermined characteristics of the users of the subgroup such that the movements of the users of the subgroup according to the movement information are located within the subspace of the subgroup, wherein the subspace of the subgroup comprises a multivariate threshold boundary such that the movements of the users of the subgroup according to the movement information are located within the multivariate threshold boundary of the subgroup, and wherein at least of the determining if the movements of the user during the physical activity are typical for the user, and the identifying a subgroup from among the plurality of subgroups that most closely corresponds to the new movement information is based on the received new external condition information;

determine if the identified subgroup is the same or different as a predefined subgroup associated with the user;

generate, in response to determining that the identified subgroup is the same as the predefined subgroup, a second output indication signal; and generate, in response to determining that the identified subgroup is different than the predefined subgroup, a third output indication signal.

2. The device of claim 1, wherein the subspace of the individualized movement profile information is a multivariate subspace, wherein the individualized movement profile information comprises a multivariate threshold boundary defining an area or region of the multivariate subspace, and wherein the determining if the movements according to the new movement information are located within the subspace involves determining if the user movements are located within the multivariate threshold boundary.

3. The device of claim 1, wherein the identifying a subgroup from among the plurality of subgroups involves comparing the new movement information to movement information of users of at least some of the plurality of subgroups using a supervised machine learning process.

4. The device of claim 1, wherein the movement information of users of a subgroup comprises a plurality of values where each of at least some of the values is an average of movement segments of a particular user of the subgroup.

5. The device of claim 1, further configured to generate or modify the individualized movement profile information for the user by receiving movement data representing a plurality of individual movement segments of the user from one or more wearable motion sensors, and using an unsupervised machine learning process on the received movement data to define an expected multivariate range of movement values for the user.

6. The device according to claim 5, further configured such that the unsupervised machine learning process generates a model based on the received movement data describing values and multivariate relationships to be considered typical for the received movement data, and the unsupervised machine learning process then defines the subspace in which movements of the user are considered typical based on the generated model.

7. The device of claim 1, further configured to amalgamate the new movement information into the individualized movement profile information of the user in response to determining that the movements of the user during the physical activity are typical for the user, and saving the amalgamated individualized movement profile information in the memory.

8. The device of claim 1, wherein the external condition information comprises information relating to at least one of terrain, route, weather, season, or time of day.

9. A method comprising:

receiving, by at least one computer processor, individualized movement profile information for a user from a database, wherein the individualized movement profile information defines a subspace in which movements of the user are considered typical for the user, and wherein the individualized movement profile information corresponds to external condition information for providing context to the individualized movement profile of the user;

receiving, by at least one computer processor, new movement information of the user relating to a physical activity from one or more wearable motion sensors;

receiving, by at least one computer processor, new external condition information associated with the new movement information;

determining, by at least one computer processor, if the movements of the user during the physical activity are typical for the user by determining if the movements are located within the subspace;

generating, by at least one computer processor, in response to determining that the movements of the user during the physical activity are typical for the user, a first output indication signal;

identifying, by at least one computer processor, in response to determining that the movements of the user during the physical activity are not typical for the user, a subgroup from among a plurality of subgroups that most closely corresponds to the new movement information, wherein each subgroup consist of movement information of users all sharing on one or more predetermined characteristics, wherein each subgroup defines a subspace associated with the one or more predetermined characteristics of the users of the subgroup such that such that the movements of the users of the subgroup according to the movement information are located within the subspace of the subgroup, wherein the subspace of the subgroup comprises a multivariate threshold boundary such that the movements of the users of the subgroup according to the movement information are located within the multivariate threshold boundary of the subgroup, and wherein at least one of the determining if the movements of the user during the physical activity are typical for the user, and the identifying a subgroup from among the plurality of subgroups that most closely corresponds to the new movement information is based on the received new external condition information;
determining, by at least one computer processor, if the identified subgroup is the same or different as a predefined subgroup associated with the user;
generating, by at least one computer processor, in response to determining that the identified subgroup is the same as the predefined subgroup, a second output indication signal;
generating, by at least one computer processor, in response to determining that the identified subgroup is different than the predefined subgroup, a third output indication signal.

10. A non-transitory computer-readable storage medium storing instructions that when executed by at least one computer cause the computer to perform operations comprising operations according to claim 9.

11. The method according to claim 9, wherein the subspace of the individualized movement profile information is a multivariate subspace, wherein the individualized movement profile information comprises a multivariate threshold boundary defining an area or region of the multivariate subspace, and wherein the determining if the movements according to the new movement information are located within the subspace involves determining if the user movements are located within the multivariate threshold boundary.

12. The method according to claim 9, wherein the identifying a subgroup from among the plurality of subgroups involves comparing the new movement information to movement information of users of at least some of the plurality of subgroups using a supervised machine learning process.

13. The method according to claim 9, wherein the movement information of users of a subgroup comprises a plurality of values where each of at least some of the values is an average of movement segments of a particular user of the subgroup.

14. The method according to claim 9, further comprising generating or modifying the individualized movement profile information for the user by receiving movement data representing a plurality of individual movement segments of the user from one or more wearable motion sensors, and using an unsupervised machine learning process on the received movement data to define an expected multivariate range of movement values for the user.

15. The method according to claim 14, wherein the unsupervised machine learning process generates a model based on the received movement data describing values and multivariate relationships to be considered typical for the received movement data, and the unsupervised machine learning process then defines the subspace in which movements of the user are considered typical based on the generated model.

16. The method according to claim 9, further comprising amalgamating the new movement information into the individualized movement profile information of the user in response to determining that the movements of the user during the physical activity are typical for the user, and saving the amalgamated individualized movement profile information in a computer memory.

17. The method according to claim 9, wherein the external condition information comprises information relating to at least one of terrain, route, weather, season, or time of day.

* * * * *